(12) United States Patent
Miethke

(10) Patent No.: US 7,766,855 B2
(45) Date of Patent: Aug. 3, 2010

(54) ADJUSTABLE HYDROCEPHALUS VALVE

(75) Inventor: Christoph Miethke, Berlin-Nuthetal (DE)

(73) Assignee: Christoph Miethke GmbH & Co. KG, Potsdam (DE)

( * ) Notice: Subject to any disclaimer, the term of this patent is extended or adjusted under 35 U.S.C. 154(b) by 808 days.

(21) Appl. No.: 11/535,242

(22) Filed: Sep. 26, 2006

(65) Prior Publication Data

US 2007/0093741 A1    Apr. 26, 2007

Related U.S. Application Data

(63) Continuation-in-part of application No. PCT/EP2005/003052, filed on Mar. 22, 2005.

(30) Foreign Application Priority Data

Mar. 27, 2004   (DE) .................. 10 2004 015 500

(51) Int. Cl.
   *A61M 5/00*   (2006.01)
(52) U.S. Cl. .......................... 604/9; 604/264
(58) Field of Classification Search .......... 604/8, 604/9, 264, 247, 248; 251/89
   See application file for complete search history.

(56) References Cited

U.S. PATENT DOCUMENTS

| 3,889,687 | A | * | 6/1975 | Harris et al. ............. 604/10 |
| 4,443,214 | A |   | 4/1984 | Marion |
| 4,676,772 | A |   | 6/1987 | Hooven |
| 4,729,762 | A | * | 3/1988 | Doumenis ............... 604/10 |
| 5,368,556 | A | * | 11/1994 | Lecuyer ................ 604/8 |
| 5,637,083 | A |   | 6/1997 | Watson et al. |
| 5,643,194 | A |   | 7/1997 | Negre |
| 5,928,182 | A |   | 7/1999 | Kraus et al. |

FOREIGN PATENT DOCUMENTS

| DE | 44 01 422 | 7/1995 |
| DE | 195 35 637 | 3/1997 |
| EP | 0 060 369 | 9/1982 |

(Continued)

OTHER PUBLICATIONS

International Search Reports (PCT/EP2005/003052 & PCT/EP03/13999) included.

*Primary Examiner*—Leslie R Deak
(74) *Attorney, Agent, or Firm*—Nils H. Ljungman & Associates

(57) ABSTRACT

Hydrocephalus valves, the valve pressure of which, when the patient is in the standing position, is determined at least partly by the weight of an additional gravitation part, are provided with an adjustable spring which partly or fully neutralizes the action of the weight. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

20 Claims, 12 Drawing Sheets

FOREIGN PATENT DOCUMENTS

| | | |
|---|---|---|
| EP | 0 421 557 | 4/1991 |
| EP | 0 617 975 | 10/1994 |
| EP | 1 380 317 | 1/2004 |
| FR | 81 05389 | 9/1982 |
| FR | 2 768 057 | 3/1999 |

* cited by examiner

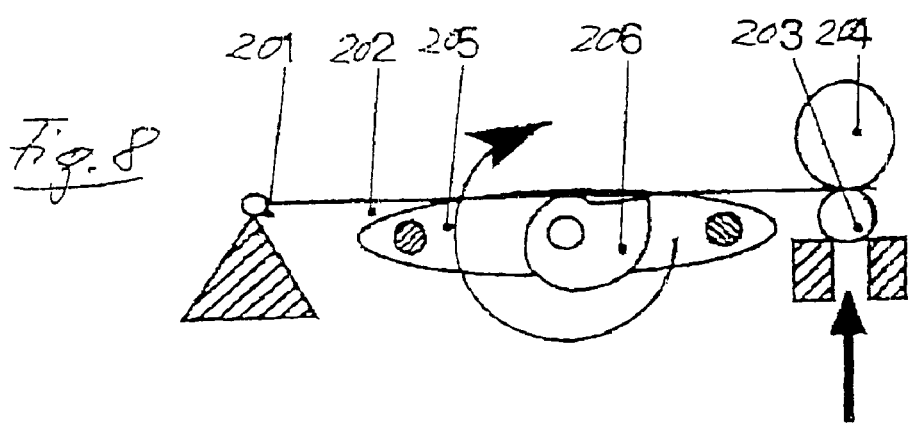
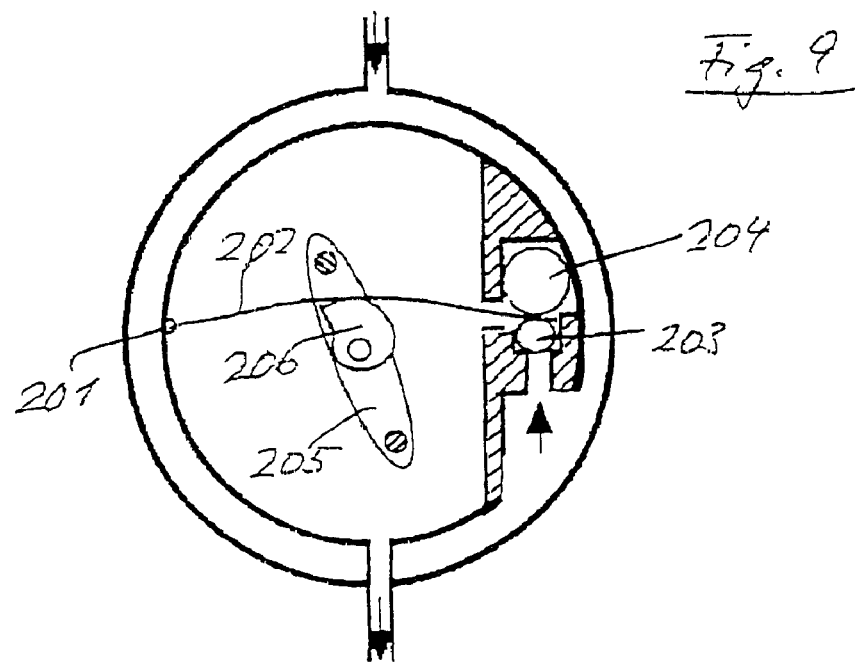

ADJUSTABLE HYDROCEPHALUS VALVE

This application is a Continuation-In-Part application of International Patent Application No. PCT/EP2005/003052, filed on Mar. 22, 2005, which claims priority from Federal Republic of Germany Patent Application No. 10 2004 015 500.3, filed on Mar. 27, 2004. International Patent Application No. PCT/EP2005/003052 was pending as of the filing date of this application. The United States was an elected state in International Patent Application No. PCT/EP2005/003052.

BACKGROUND

1. Technical Field

This application relates to an adjustable hydrocephalus valve to equalize the pressure of the liquor in the cranium of a hydrocephalus patient.

2. Background Information

Hydrocephalus patients have the following medical problem: The brain is surrounded by a special liquid called liquor. This liquor is continuously being produced and reabsorbed in equal amounts. In the illness hydrocephalus (also called water on the brain), this equilibrium is disrupted and more liquid is produced than is reabsorbed. Because the interior of the skull represents a closed vessel, the result is an increase in volume. In infants, the seams in the skull cannot grow together and close, and in adults the internal pressure in the skull increases. Therefore there are two varieties of hydrocephalus: adult and infantile.

Hydrocephalus treatment initially consisted of simply draining the liquor. This drainage was effected by means of a simple hose connection between the skull and a large blood venous blood vessel or by a corresponding connection between the skull and the abdomen via a hose. It was quickly determined, however, that the pressure in the skull must maintain a certain physiological value if other complications are to be prevented.

In the treatment of hydrocephalus, implantable drains are used to create an artificial connection between the ventricles of the brain in the head and a drainage compartment, which is currently most often the abdomen.

A number of different types of valves are known that are installed in the drain for the liquor, and by means of which the pressure of the liquor can be set. Valves of this type are implanted under the skin in the vicinity of the head. The valves are designed to open at a certain critical pressure and to release the flow of liquor. By means of a line—which is also implanted under the skin—the liquor is drained into the upper vena cava or into the abdominal cavity.

The valves of the prior art help considerably, of course, but a satisfactory solution has not yet been achieved with the valves of the prior art.

For example, valve developments are disclosed in the prior art that make possible a percutaneous, non-invasive adjustment of the opening pressure.

The valves in question are implanted in the patient and preferably drain the excess liquor from the patient's skull via a hose, which is likewise implanted, and empty into the vena cava or into the abdomen. The valve pressure is thereby determined by a spring, whereby the spring is adjusted by means of a mechanism that has a pivoting or rotating part that is moved from outside by pivoting or rotating an integrated magnet, so that the tension on the spring is increased or relaxed.

The valves of the prior art have a more or less flat construction. The objective of the flat construction is to prevent bumps or protuberances on the patient's head to the maximum extent possible as a result of the implant procedure.

The best-known valves include the Codman Medos valve (U.S. Pat. No. 5,928,182).

This valve is a ball valve with a spring-loaded ball. The valve is adjusted by changing the position of the spring. The spring presses with one end on the valve ball. With the other end, the spring is braced against an abutment. In this model, the height of the abutment can be adjusted by rotation. The height can be adjusted because the abutment is rotational and is provided on top with an inclined edge along which the spring glides.

Patent Application EP 1380317 A1 teaches an improvement for this valve, by means of which an unintentional adjustment of the rotor and consequently of the opening pressure can be prevented. In this patent, a clip that is integrated into the silicone jacket is engaged laterally with the rotor, to effect a lateral clamping of the rotor and to prevent the unintentional adjustment of the valve. The function of a construction of this type is somewhat doubtful, however, because in actual use, the housing is carrying a flow of a watery solution (liquor). The sliding characteristics between silicon and the rotor are thereby unfavorably altered. The elastic tension is insufficient to guarantee a friction-tight protection against twisting.

The valves of the prior art also include the Sophysa valve (Patent No. FR 8105389; EP 0060369; U.S. Pat. No. 4,443,214).

Even the manufacturer of this valve warns that the hydrocephalus patient should avoid touching permanent magnets in toys, headsets, loudspeakers and electromagnetic fields of the type that are emitted by electric motors, electric shavers, hair dryers, switches etc. This warning from the manufacturer is tantamount to a warning against being around most of the things people come in contact with in everyday life. Since it is practically impossible for a modern human being to avoid contact with such things, proposed solutions of this type are simply impractical. The manufacturer has recently introduced an improved version of this valve to the market (U.S. Pat. No. 5,643,194). This new model, in fact, does provide some protection against unintentional adjustments. Two radially movable magnets that sit on a rotational rotor are arranged so that they attract without any external action and thereby block the rotor in notches created on the housing. Stronger magnets that are applied externally can then overcome the attractive forces on the valve side and pull the magnets apart radially. As a result, the rotor is unlocked, and by rotating the rotor by rotating the externally applied magnets around the axis of the rotor, it becomes possible to adjust the opening pressure. This principle has in fact shown itself to be susceptible to failure in actual practice. Although unintentional rotation is prevented, the intended adjustment is frequently unsuccessful. This problem can be traced to the difficulty of reliably determining the exact position of the valve, because in actual use, friction forces that are difficult to calculate interfere with or even totally prevent the movement of the sliding magnets inside the valve. An additional disadvantage is that because the layers of skin at these points can be rather thick, the two sliding magnets must be pulled far apart, whereby the forces resulting from the externally applied magnetic field become exponentially smaller as the distance increases, and in any case are then no longer sufficient to pull the magnets apart. A simplification and improvement of this arrangement is necessary and desirable.

The principle of a magnetic clamping of a rotationally mounted rotor, which was disclosed as long ago as U.S. Pat. No. 4,676,772 in 1987, has never established a foothold in the market. Here, too, the extremely problematic technology of a 100% magnetic brake in a hydrocephalus valve also becomes apparent. By means of extremely small magnets that are integrated into a rotational flat disk, on which two pins are oriented parallel to the axis of rotation and are inserted into a threaded portion that contains a ball that can rotate along a thread, the height of the threaded portion can be adjusted, as a result of which the force that is exerted against the ball by a silicone membrane can be reduced or increased. To rotate the adjustment disc, first the attractive force between the magnets integrated into the disc and a ferromagnetically active housing part must be overcome by strong magnets that are applied externally. The disc is thereby lifted up slightly, so that rotation becomes possible. This principle has never been found to be either practical or reliable. In particular, the many small moving parts contribute to a critical addition of disruptive friction forces, which cannot be controlled, for among other reasons on account of the small size of the valve and also as a result of the magnets used. The pins can very easily tip out of alignment, and the friction in the threads that is applied externally with a long lever arm is almost impossible to overcome with the very weak magnetic field derived from the small magnets. The thread must also have some play to allow smooth movement, which in turn is disadvantageous to the accuracy of the adjustment. The location of the valve is also problematic here, and an exact adjustment is practically impossible to achieve on account of the small size of the parts that have to be moved. Because of the use of a silicone membrane, the reproducible setting of the opening pressure is impossible, because the properties of the material vary incalculably. For the reasons indicated above, this design has not yet reached a stage where it is ready for the market.

An additional system is offered by Medtronic/OS-Medical (U.S. Pat. No. 5,637,083). Here too, this system teaches that the opening characteristic of a valve can be manipulated through the skin by the rotation of a rotor into which two magnets are integrated. The patent teaches an unintentional adjustment can be prevented by a mechanical pin that must be deactivated percutaneously. However, clinical use has made it clear that the pin can cause a critical jamming of the rotor. The manufacturer was forced to withdraw this unreliable technology from the market and thereafter market the valve without the mechanism to prevent the unintentional adjustment. The danger of the unintentional adjustment therefore remains present, in particular when the requirement for the ability to reliably adjust the valve is taken into consideration.

An additional disadvantage of the system of the prior art is that the adjustment must be effective both in the standing position as well as in the reclining position. However, this is a characteristic that is frequently undesirable. The setting of a characteristic valve pressure that becomes effective only when the patient is in a standing position is both therapeutically logical and helpful. On account of the hydrostatic pressure differential that occurs only when the patient is in a standing position—in particular with the ventriculo-peritoneal drain—in the systems that have been available up to now, as described above, it is of course possible to counteract the complications that result from excessive drainage caused by an elevation of the opening pressure, although at the same time a desired, appropriate draining of cerebrospinal fluid when the patient is lying down—as could be ensured by a low setting of the opening pressure—is systematically prevented.

The consequence for the patient is a physiologically uncomfortable pressurization of the ventricle of the brain immediately after standing up, which can lead to discomfort and dizziness as well as to serious complications such as subdural effusions and bleeding that must be treated by surgery. It is not possible to prevent such complications with the valves described above. Of course, by turning up the valve, the negative pressure in the standing position can be modified in a positive direction, although simultaneously the increased pressure also acts in the reclining position, where it is altogether inappropriate. The higher setting therefore on one hand reduces the undesired extremely negative pressure in the standing position, but at the same time it prevents a therapeutic effect in the reclining position, in particular when the patient is resting or sleeping.

OBJECT OR OBJECTS

The object of at least one possible embodiment is to eliminate or virtually eliminate these disadvantages of the adjustable valves of the prior art. The application teaches that this object can be achieved with at least one possible embodiment disclosed herein. The particular object of the application is to make a valve adjustment possible only when the patient is in the standing position or in partly diagonal positions, which valve adjustment has no influence on the setting when the patient is in the reclining position.

SUMMARY

The starting point of at least one possible embodiment is thereby a conventional gravity-activated valve, e.g. of the type described in Patent No. DE 4401422, Christoph Miethke. Gravity valves use the weight of one or more metal balls, preferably made of tantalum, to counteract the pressure differential that occurs in the drainage line as a function of the position of the patient to prevent undesirable and excessive drainage. These valves conventionally have a ball as a closing part. There are also other types of closing parts. When the patient is in the standing position, the full pressure of gravity is exerted. When the patient is in the reclining position, the gravitational pressure has no effect. In intermediate positions, the gravitational pressure is only partly active.

The application teaches that the gravitation pressure of the valve is neutralized in whole or in part by an adjustable spring mechanism in the standing position. This principle can be implemented in different ways. Preferably the movable closing part is combined with a movable and adjustable gravitation part which forms an adjustable load for the closing part. The result is an advantageous freedom of design. An optimal distribution of weight between the closing part and the gravitation part can also be achieved. As a rule, the optimum lies at a low weight of the closing part and a weight of the gravitation part that is several times greater.

The closing part can be in one of several different shapes. In the solutions of the prior art, balls are used exclusively. The ball forms a very reliable closing part. The gravitation part, however, can also be in a number of different shapes. The application teaches that the shape of the gravitation part can be, among other things, a ring, a disc or a bell.

The gravitation part can optionally be formed by a second ball. The ball that forms the gravitation part is preferably several times larger than the ball that forms the closing part. The weight of the ball that forms the gravitation part is thereby increased. The weight of the gravitation part can also be influenced by the choice of a material with a higher density.

In the embodiment with a second ball that forms the gravitation part, when the patient is in the standing position the balls are located one above the other.

The upper ball is preferably made of a heavy metal material with a high specific weight (the use of tantalum is particularly advantageous in this case), and the bottom ball is made of the lightest possible ceramic material, as a result of which the weight of this ball by itself exerts only a very minimal opening pressure, which is typically 1 cm WS (column of water). Titanium has a low weight that is comparable to that of tantalum.

The application teaches that a spring is preferably engaged with the upper ball. The spring can be a leaf spring that is engaged between the balls. The spring can be adjusted so that when the patient is in the standing position, the weight of the upper ball is absorbed in its entirety by the leaf spring. This situation can be altered by adjusting the spring.

When the patient assumes the reclining position, the two balls lose their gravitational effect. The two balls release the valve opening.

With the adjustment, the valve can very easily be adjusted to changing conditions that result from growth, weight gain or for other reasons, including therapeutic reasons.

The two balls are optionally located in a guide which is formed by cylindrical borings. In the guide there is a sufficiently large opening for the leaf spring.

The gravitation part is optionally in the shape of a disc, a ring, a cap or a bell. This design opens additional possibilities for the design of the gravitation part. The disc can utilize the maximum extension of the valve housing. When the valve has a flat disc shape, the valve housing has its largest dimension along the flat side, which means that a desired flat construction becomes possible.

The application teaches that the disc, in spite of its low thickness, can easily have the desired weight on the basis of its large size. The same can be said for a ring-shaped configuration of the gravitation part. The ring can enclose other valve parts and thus lead to a compact design.

The advantages of the disc and of the ring can optionally be combined in the shape of a cap or a bell.

The cap shape preferably has a cylindrical jacket and a flat, disc-shaped cover. The bell shape optionally has a conical jacket. Titanium is a suitable material, and for a compact construction, tantalum is the ideal material.

The gravitation part of at least one possible embodiment can be realized in the form of a disc, ring, cap or bell and is preferably located so that it can pivot in the housing. The pivoting arrangement forms an advantageous guide for the gravitation part, because a minimal friction can be realized during the movements of the gravitation part that are induced by the change of position, whereby the friction generated has an adverse effect on the precise adjustment of the valve. Preferably the position of the axis of pivoting is selected so that the gravitation part presses centrally on the valve ball that forms the closing part. When the patient is in the standing position, the gravitation part preferably presses vertically on the highest point of the valve ball that forms the closing part. During the pivoting movement of the gravitation part of at least one possible embodiment, the gravitation part should move the shortest possible distance possible from the vertical. For this purpose the axis of pivoting is oriented so that when the patient is in the standing position, the axis of pivoting is at the greatest possible distance from the vertical that runs through the highest point of the ball used as the closing part.

The axis of pivoting can be firmly connected with the gravitation part and can be mounted so that they can pivot or rotate in the valve housing. As in the exemplary embodiment, it is advantageous to fix the pivoting gravitation part to the axis.

The valve can be adjusted extremely reliably. One way includes a special adjustment of the spring. In this case, the adjustment travel that is converted into a variation of the spring load is particularly large. In other words, with a comparable range of variation of the spring load, the adjustment travel provided is greater. To the extent by which the adjustment travel is greater, the above mentioned risk of an unintentional adjustment is reduced. The accuracy of the adjustment is simultaneously increased as the adjustment travel becomes greater.

The other way to achieve greater reliability is realized by the magnetically-activated Belleville spring washer that is integrated into the housing which locks the rotor in position and prevents any undesirable adjustment.

The possibility of making the adjustment travel greater results from a change in the position of the spring. The application teaches that the spring is designed so that the plane of movement of the spring, during its adjustment, lies parallel to the plane in which the pivoting or rotational movement of the spring takes place. The application teaches that this parallelism is also present when the planes coincide.

As a result of the location and orientation of the spring of at least one possible embodiment, the spring can move in the direction in which the valve housing has the largest dimension, i.e. in the direction of the flat side.

The spring used is preferably a spring steel bar. The spring steel bar can have different cross sections, e.g. a small, round cross section. In that case we are talking about a wire spring. It can also have a flat, broad cross section, in which case we speak of a leaf spring. The spring steel bar is located so that it can pivot and acts as a lever arm. Preferably a one-armed lever is used, the one end of which is mounted so that it can pivot in the valve housing and the other end of which is engaged between the above mentioned balls. The spring adjustment mechanism is engaged with the spring between the two ends.

The spring can optionally also form a two-armed lever, the one arm/end of which is longer than the other arm/end. Optionally, the shorter or longer end is engaged with the valve balls. The other end interacts with the adjustment mechanism described above. In that case there is an effective sliding connection, which is itself known from the prior art, between the spring and the rotational or pivoting adjustment mechanism. In other words, the spring slides on a surface of the rotating or pivoting part of the adjustment mechanism.

The effective connection with the closing part that is realized in the form of a ball or flap is thereby formed as a result of the fact that the shorter end presses in a sliding fashion against the closing part. The effective connection with the adjustment mechanism depends on the configuration of the adjustment mechanism. Preferably, the adjustment mechanism provided is a rotation device or pivoting device which is provided with a sliding surface and interacts with a sliding surface of the spring. The effects of an adjustment depend on the configuration of the spring.

The spring can form a two-armed lever. In that case, the one end of the spring is preferably effectively connected with the gravitation part and the other end is connected with the adjustment device, and the spring is mounted between them so that it can pivot in the valve housing.

If the spring forms a two-armed lever, and if the lever arms are of different lengths, it then becomes a question of where the adjustment mechanism is engaged.

If the adjustment device is engaged on the short lever arm, the adjustment movement effects a greater deformation of the long lever arm of the spring. If the adjustment device is engaged on the long lever arm, the adjustment movement effects a lesser deformation of the short lever arm.

The force with which, when the patient is in the standing position, the spring relieves the closing part from the weight of the gravitation part is a function of the magnitude of the deformation of the spring.

Optionally, the spring can also be realized in the form of a one-armed lever. This configuration occurs if the spring is effectively connected on one end with the gravitation part and is mounted on the other end so that it can pivot, and if the adjustment device is engaged on the spring in between.

The adjustment device for a sliding connection is preferably realized with the spring on the sliding surface in the form of a curved track.

The curved track preferably runs at least partly in a spiral shape on the pivoting or rotating part. The peripheral angle on the pivoting or rotating part is preferably at least 300 degrees. The spring can slide upward or downward on the curved track. The direction of movement results from the direction of rotation or the direction of pivoting of the rotating or pivoting part.

Optionally, the rotating part can also be moved farther in the same direction of rotation and nevertheless come back to the starting point of the adjustment. The application teaches that this capability is achieved because a connection is provided between the beginning of the curved track and the end of the curved track on the rotating or pivoting part.

The spring of at least one possible embodiment optionally has an angular shape. The two lever arms of the two-armed lever are at an angle with respect to one another that is less than 180 degrees, and can even be less than 90 degrees.

The cross section of the spring taught by the application can be whatever is desired or most appropriate. Round and rectangular shapes are advantageous. A spring with a leaf-shaped or wire-shaped cross section is particularly advantageous.

For the pivoting and/or rotating mounting of the spring it is appropriate, for example, to use a pin, the ends of which are engaged in corresponding recesses in the valve housing or in the valve cover. The ends of the pin can also be sharp, so that the pin rotates on the tips in the recesses. This method is technically and economically advantageous.

For fastening the pin to the spring, a welded or soldered connection is appropriate, although other types of connections can also be used. Other mechanical connections such as clamp connections and plug-in connections can also be considered.

For the function of the spring of at least one possible embodiment, it can be advantageous if the long lever arm is guided on the pivoting part or the rotating part of the adjustment mechanism. For this purpose, this part can also guide the spring on at least one side. On the other side, the guide can be formed by a disc.

When a valve ball is used as the closing part, it is advantageous on the valve ball side if there is a large surface area available for contact between the spring and the valve ball. If the spring does not permit this contact over a large surface area, a metal sheet can also be fastened to the end of the spring in question. The metal sheet can be optionally welded or soldered or fastened in any other appropriate manner.

Various systems can be used to secure the adjustment device in the current rotational position. Purely mechanically acting brakes can be used. Preferably a self-activating brake is used, which is created by clamping the adjustment device friction-tight in the valve housing after each adjustment movement. For any further adjustment, the valve housing is deformed so that the valve housing with its friction surfaces lifts up from the corresponding friction surfaces of the adjustment mechanism. The required deformation is created by pressure. In one prior art document, the friction surfaces can be located on the sides of the valve housing. In another solution of the prior art, the friction surfaces are located elsewhere, namely directly on the bottom or cover of the valve housing or on a part of the adjustment device that interacts with the bottom or cover of the adjustment device. By depressing the bottom or cover, the adjustment device is released so that an adjustment can be made. When the depression force on the bottom or cover is released, the bottom or cover returns to its original shape, and the friction-tight connection between the cover or the bottom and the adjustment device is re-established.

According to another concept of the prior art, the adjustment device can also be secured in the current rotational position by means of magnets. Magnets and/or permanent magnets can thereby be located on the adjustment device and/or on the inside of the housing. The magnets form a part of an arresting device. The arresting device can also include other moving parts that engage in arresting holes or in gear teeth as the result of the application of a magnetic force. The arresting effect can be overcome, however, by the use of stronger magnets. The use of reactive materials, e.g. steel or also magnetic material, is advantageous for the magnets.

In addition, it is advantageous to select the friction surfaces so that a particularly strong self-locking action is achieved. For that purpose, the application teaches that a minimum distance is provided between the friction surfaces and the axis of rotation or the pivoting axis of the rotating or pivoting part. Preferably, the friction surfaces are at the greatest possible distance from the center of the valve on the outer edge of the rotating or pivoting part of the adjustment device.

The magnets used are preferably of small size and in the form of pin magnets, as described in the claims. The small magnets also contribute to the small dimensions of the valve, as described in the claims.

The adjustment device for the valve of at least one possible embodiment can also be designed with extremely small dimensions. The application teaches that this feature is used to reduce the diameter of the adjustment device and to achieve a special shape of the adjustment device, namely in a shape similar to that of a ball-point pen. This form makes it possible to handle the adjustment device like a pencil or a ball-point pen. Instruments of this type can even be carried in a breast pocket. Simultaneously, the mechanism of a ball-point pen is used to use the magnets provided in the head of the instrument for the measurement of the pressure that has been set, and/or to set the pressure. A mechanism similar to the one in the ball-point pen is used to extend or retract the writing tip. In this case, that capability is used to connect the magnetic drum friction-tight with the adjustment unit or to loosen it. If the connection is detached, the instrument acts as a measuring pin. If the connection is intact, it works as an adjustment pin.

The pen-shaped adjustment device of at least one possible embodiment has, on its front end, a cap with which the adjustment device is attached. When the adjustment device is attached loosely, the magnets automatically effect a centering of the adjustment device, so that it is easy to actuate the adjustment device by rotating it.

After the centering of the adjustment device, there is preferably an elastic deformation of the valve. The deformation is achieved by a controlled pressing of the adjustment device on the implanted valve. The application teaches that the deformation leads to a lifting of the pivoting or rotating part away from the valve housing. The friction is reduced accordingly. The friction is reduced to a minimum, which is referred to as a neutralization of the friction.

After the neutralization of the friction, the pivoting or rotating part on the valve side can be easily moved with the adjustment device and can assume its desired position.

The above-discussed embodiments of the present invention will be described further hereinbelow. When the word "invention" or "embodiment of the invention" is used in this specification, the word "invention" or "embodiments of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

FIG. 8 shows a schematic diagram of a closing part and a gravitation part, together with a spring system and an adjustment device;

FIG. 9 shows a schematic illustration of a valve housing into which the system illustrated in FIG. 8 is integrated;

DESCRIPTION OF EMBODIMENT OR EMBODIMENTS

Figure 5:
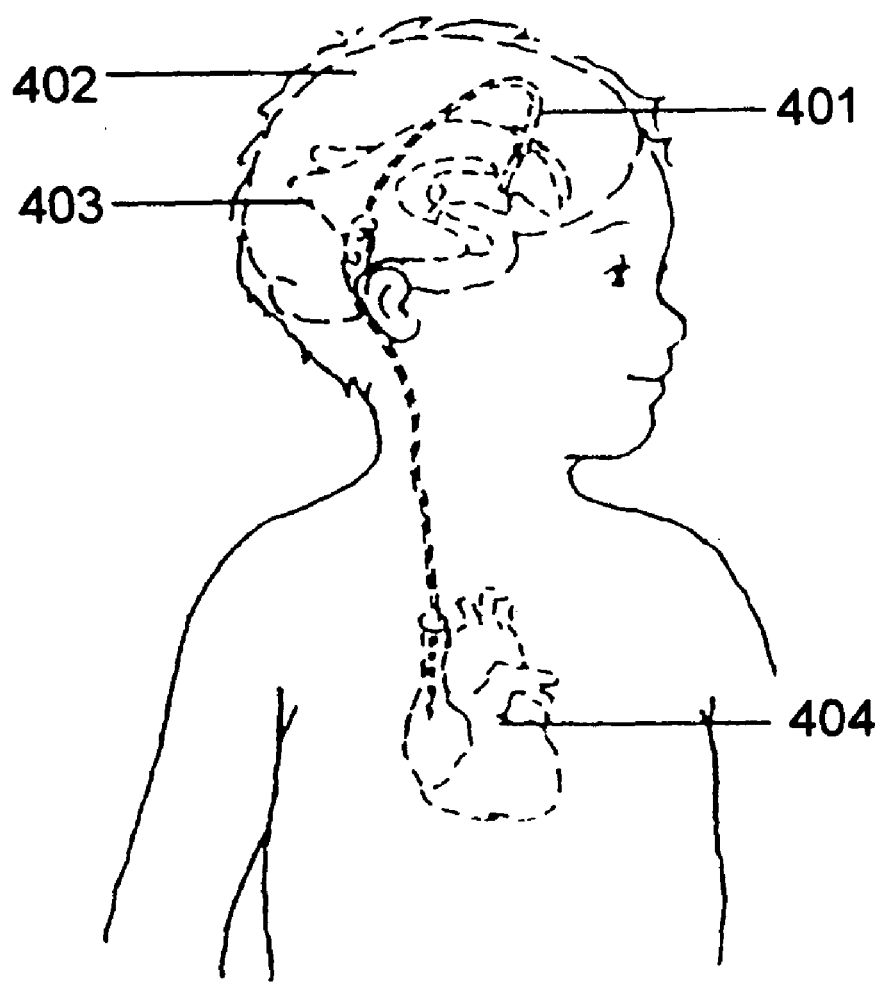
FIG. 5 shows an example of a hydrocephalus treatment device connected to a patient.

FIG. 5 shows an example of a hydrocephalus treatment device connected to a patient. The device comprises a ventriculo-atrial (VA) shunt 401. The VA shunt 401 moves cerebrospinal fluid from the ventricles 403, or spaces in the brain 402, into the atrium, or top chamber, of the heart 404 through a vein in the neck.

Figure 7:
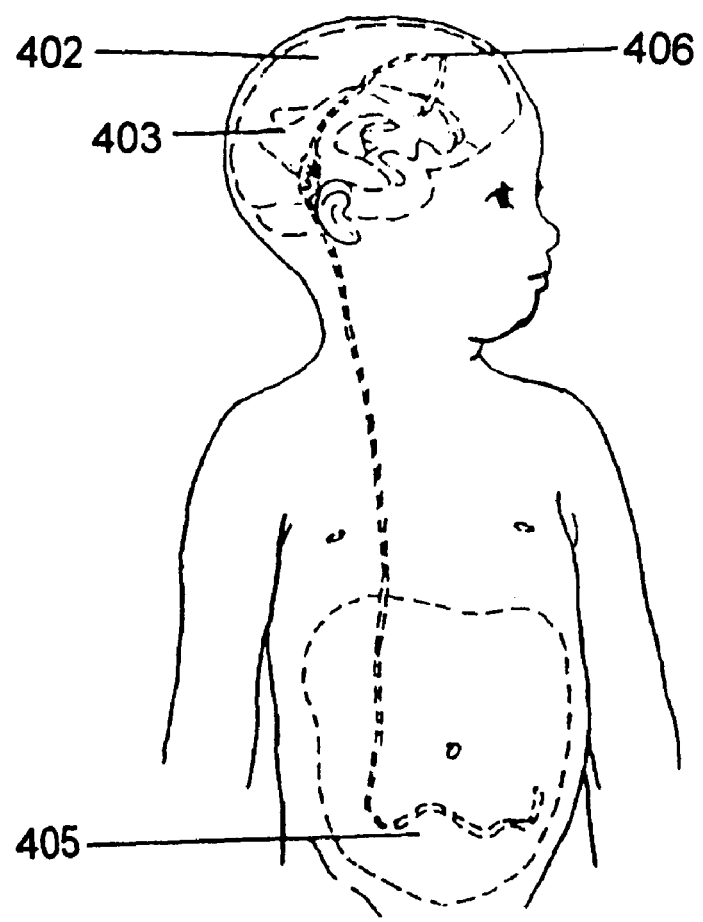
FIG. 7 shows another example of a hydrocephalus treatment device connected to a patient.

FIG. 7 shows an example of a hydrocephalus treatment device connected to a patient. The device comprises a ventriculo-peritoneal (VP) shunt 406. The VP shunt moves cerebrospinal fluid from the ventricles 403, or spaces in the brain 402, to a space in the peritoneal cavity inside the abdominal cavity 405.

Figure 10:
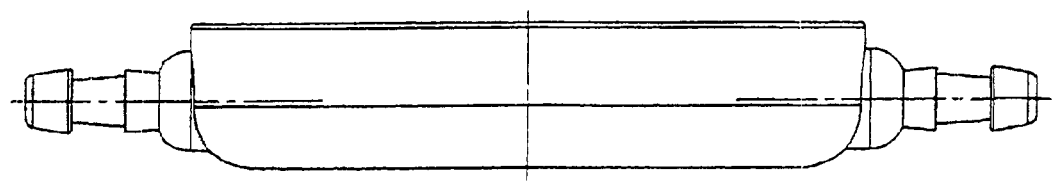
FIG. 10 shows the exterior of at least one possible embodiment of a hydrocephalus valve.
Figure 12:
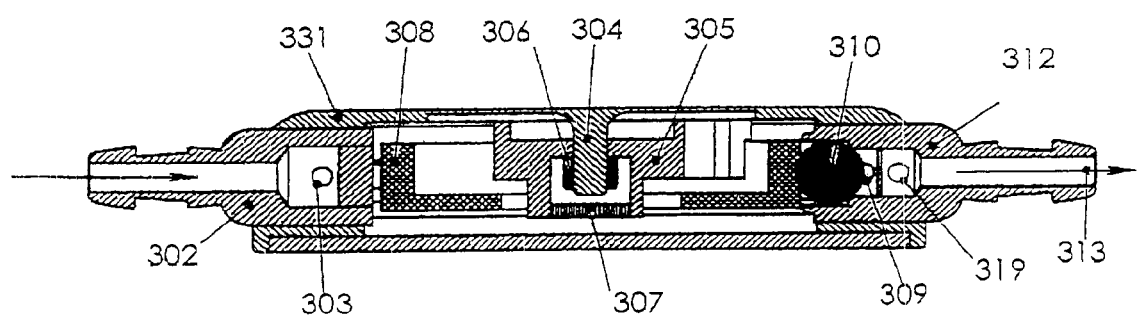
FIG. 12 shows another cross-sectional view of the interior of the hydrocephalus valve of FIG. 10.
Figure 11:
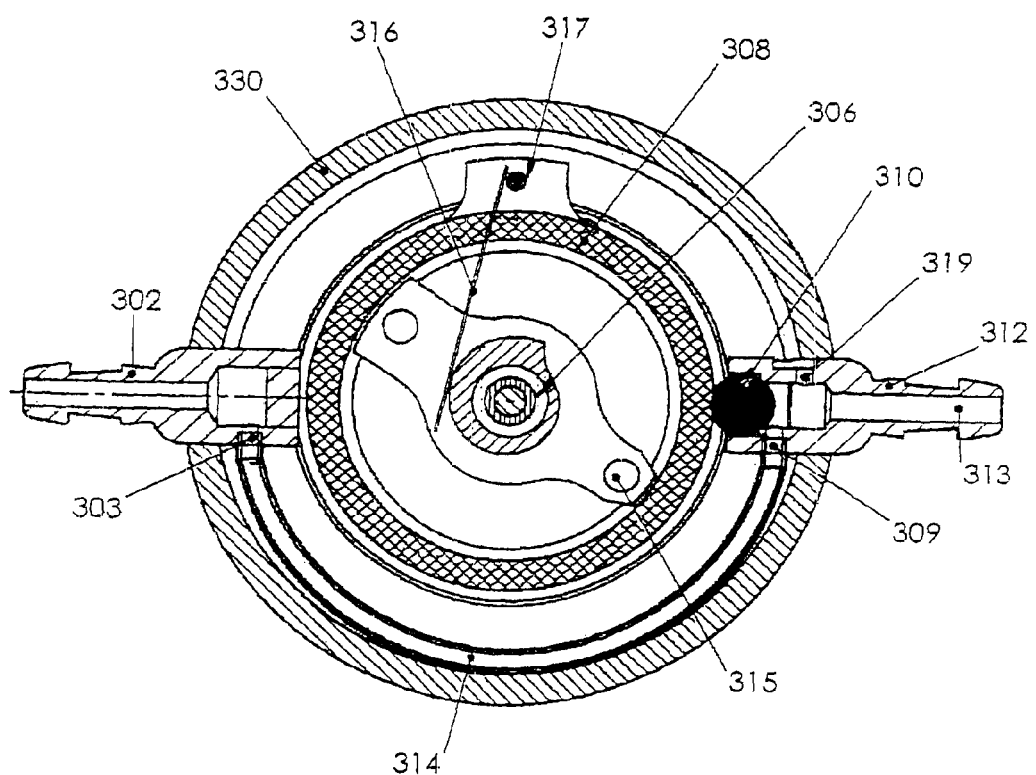
FIG. 11 shows a cross-sectional view of the interior of the hydrocephalus valve of FIG. 10.

In the accompanying drawings, FIGS. 10, 11 and 12 illustrate one exemplary embodiment.

The valve comprises a solid metal housing 330. In the exemplary embodiment, the valve also includes a valve ball 310 as the closing part of the valve, a gravitation part 308 to produce an elevated closing pressure in the valve, a spring system 316 with an adjustment device and an arresting device. The valve is located in a liquor line which is implanted in a hydrocephalus patient. The valve is designed to promote the flow of the excess liquor when the patient is in the reclining position, while when the patient is in a standing position, the discharge of the liquor is made more difficult by an elevated closing pressure of the valve.

FIG. 8 shows a schematic diagram of a closing part and a gravitation part, together with a spring system and an adjustment device.

Integrated into a valve housing, which is not shown in FIG. 8, is a link 201, to which a pivoting spring in the form of a leaf spring 202 is fastened. The side of the spring facing the link 201 rests on a valve ball 203, which is either an immediate component of the valve seat and is made of sapphire or ruby or another ceramic material, although it can also be made of titanium. Located above the ball 203 is an additional ball 204 in the form of a gravitation part of the valve. This latter ball is a metal ball. Suitable metals include tantalum or stainless steel, for example. Basically, however, all biocompatible materials with the highest possible density are suitable. The spring 202 is engaged between the two balls 203 and 204. A magnetically activated rotor 205 is attached between two contact points of the pivoting spring 202. In the center of the rotor is a cam 206 which is firmly connected to the rotor. The rotor can be rotated by external magnetic fields. The external magnetic fields can be generated electrically or can be produced by permanent magnets.

When the rotor is adjusted, it leads to a deformation of the leaf spring between the pivot bearing and the point of contact with the ball. As a result, a spring force is generated that acts against the gravity of the weight ball.

FIG. 9 shows a schematic illustration of a valve housing into which the system illustrated in FIG. 8 is integrated. The liquor enters from above and flows through a channel in the valve housing toward the valve ball 203, which when the patient is in the standing position bears the weight of the ball 204.

The valve position illustrated in FIG. 9 shows the setting of the minimum opening pressure. In the valve, the opening pressure is determined by the gravitation force of the ball 204, the opening cross section at the inlet below the sapphire ball 203 and by the spring force that has been set and acts counter to the gravitation force. In the illustrated valve position, the adjustment device has reached the maximum position. That is equivalent to a maximum deformation of the spring and a maximum relief of the load on the gravitation part 204. This spring force could be designed so that at the maximum spring bias, it compensates for all or some of the gravitation force.

Figure 1:
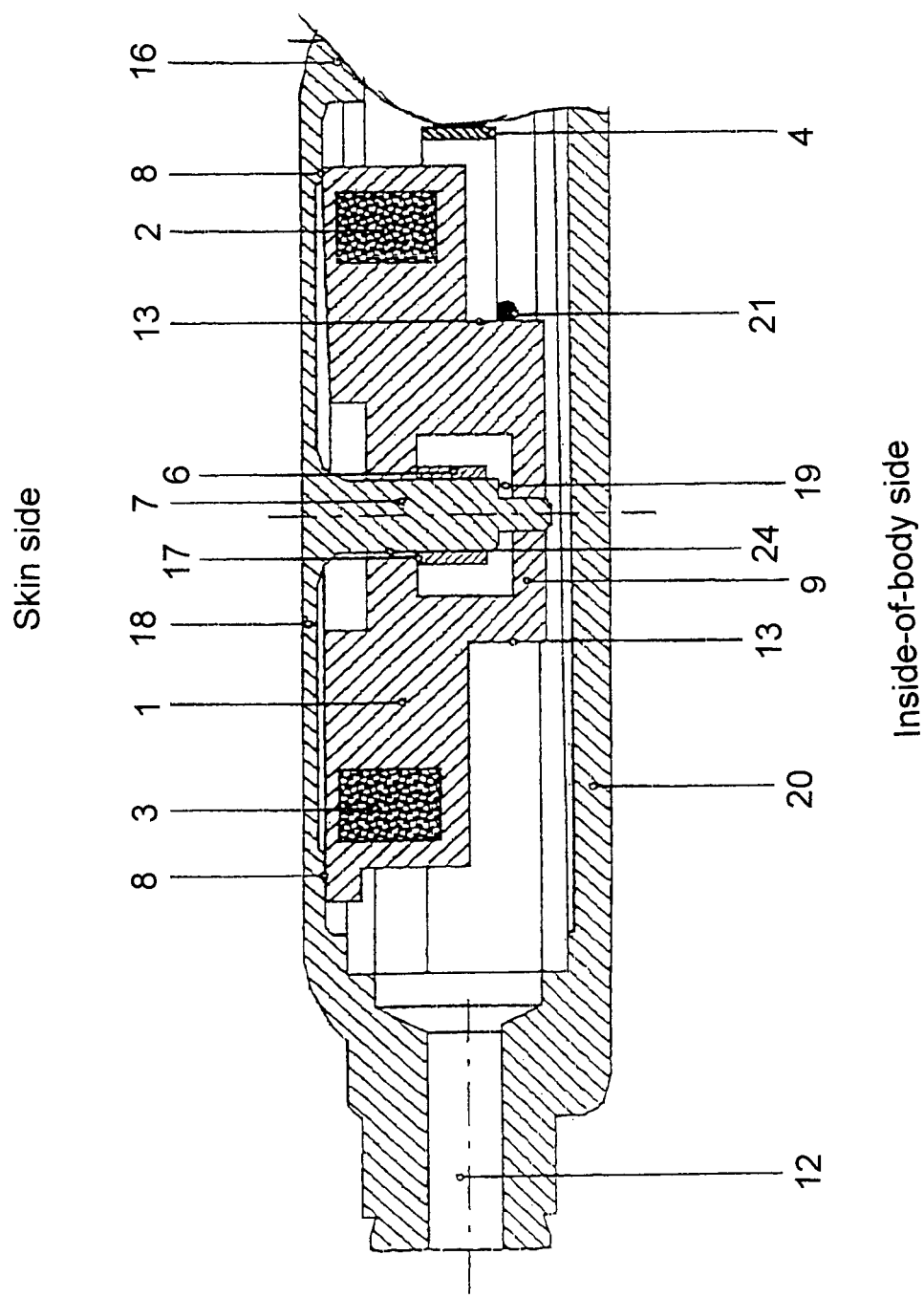
FIG. 1 shows a section through a housing with a spring system and an adjustment device.
Figure 1A:
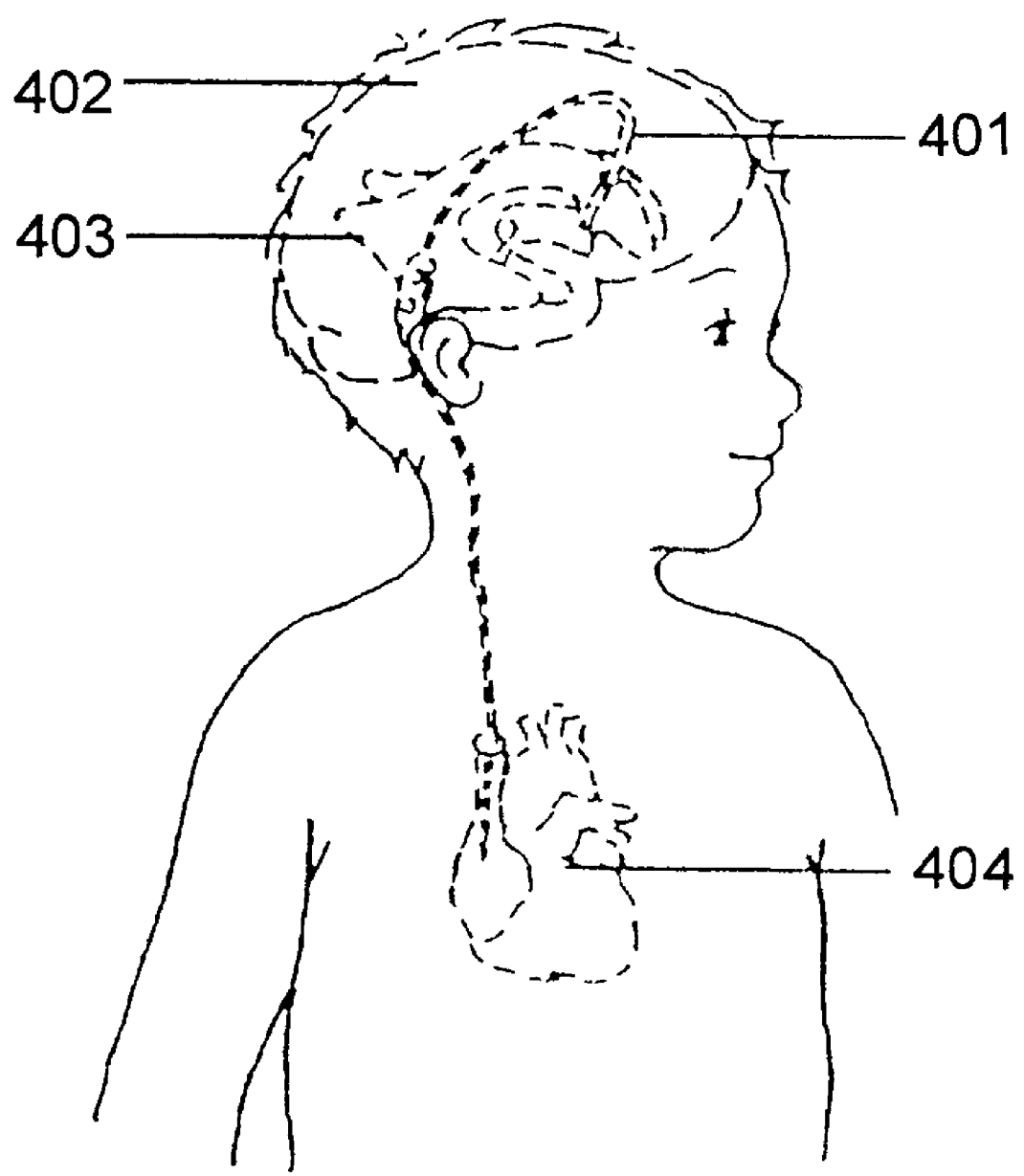
Figure 1B:
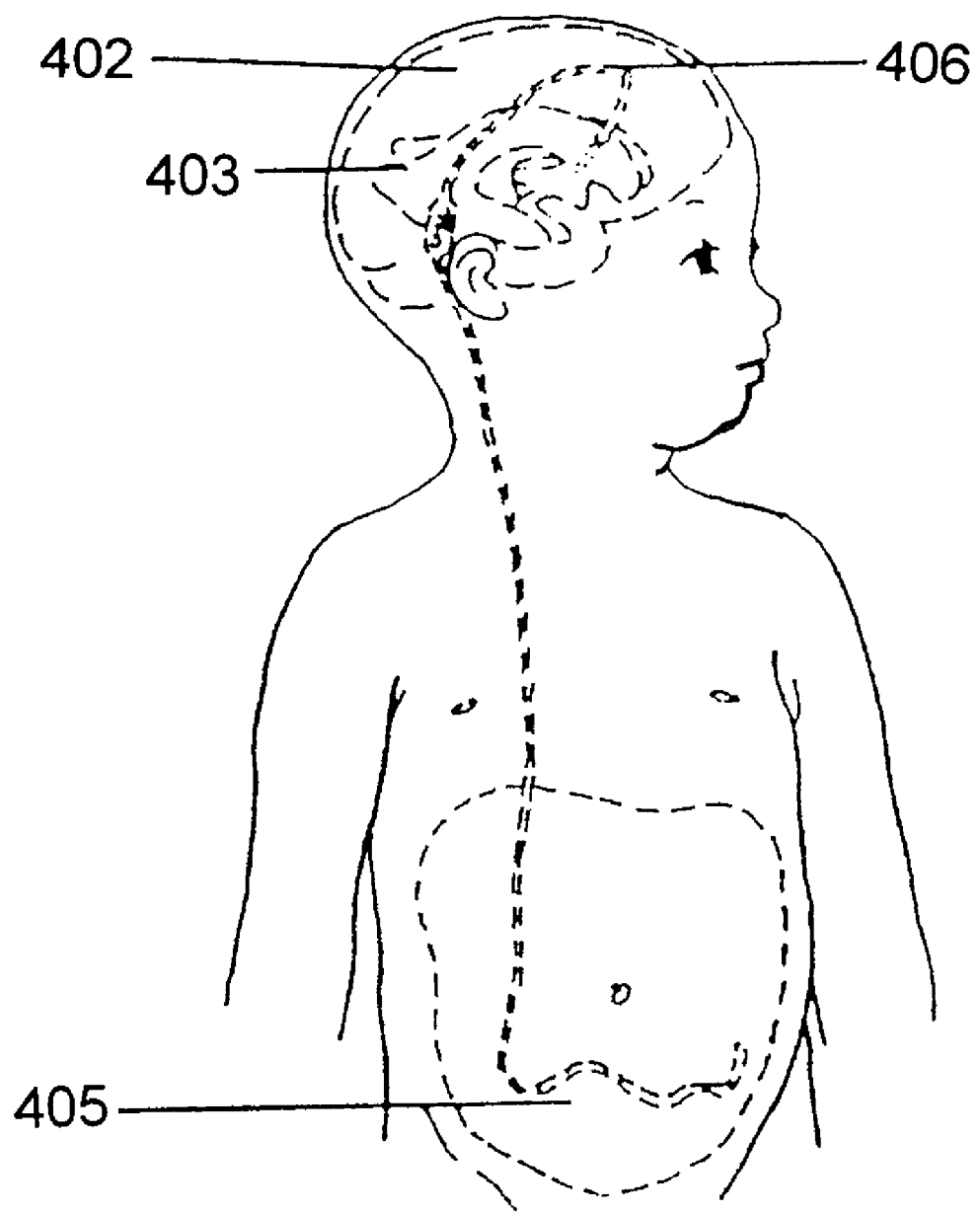

To illustrate the operation of the brake, FIG. 1 shows a larger section through a housing with another spring system and another adjustment device and in greater detail than in FIG. 9. The valve comprises a solid titanium housing 16. The valve housing 16 is in the shape of a ring and is closed on both sides by cover 18 and 20.

Figure 2:
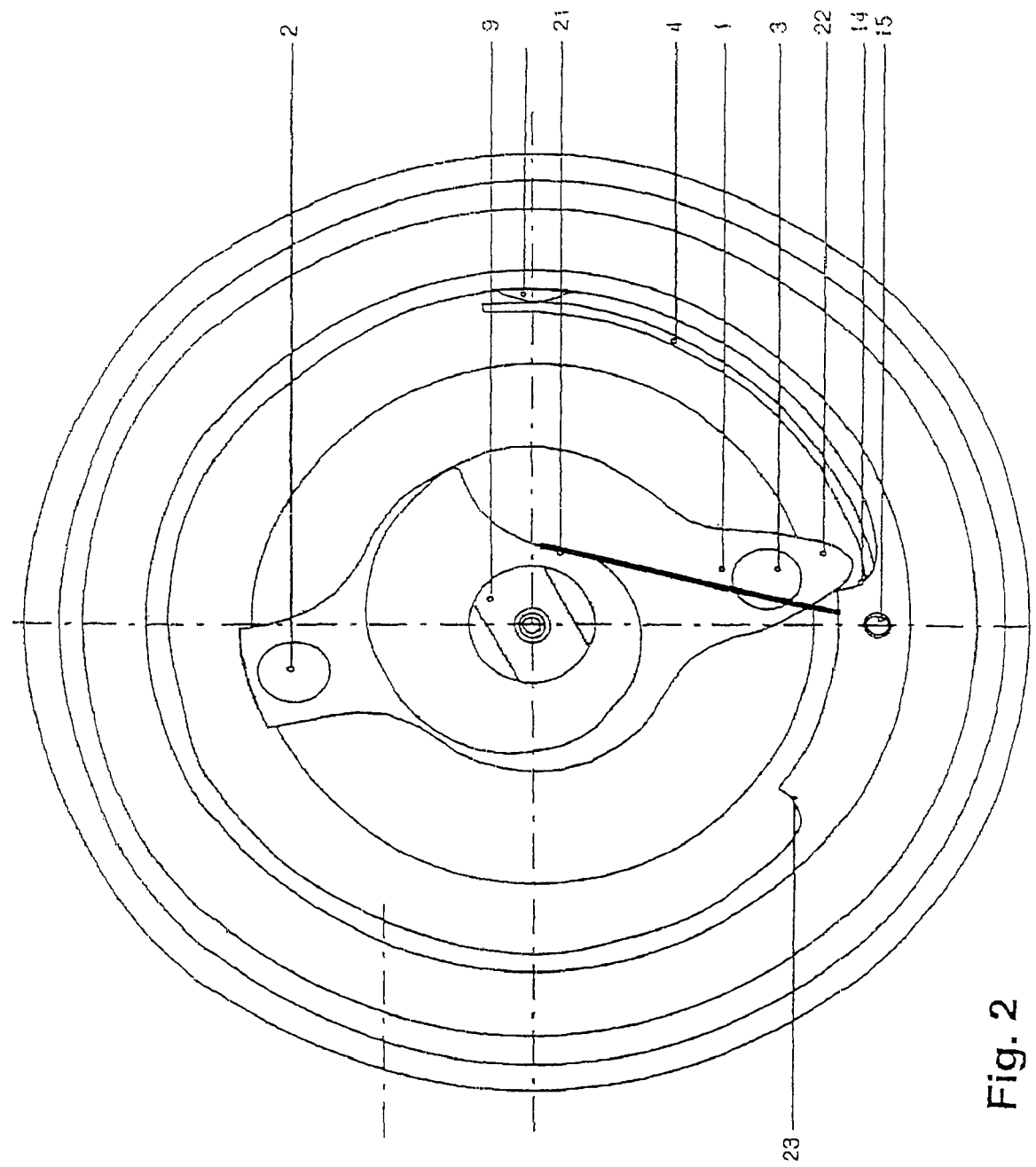
FIG. 2 shows another section through the housing, to show the spring system and the adjustment device.

FIG. 2 shows another section through the housing, to show the spring system and the adjustment device. The spring system includes a leaf spring 4.

The leaf spring 4 forms a functional unit with the spring wire 3 and a shaft 15 which is visible in FIG. 2. In the valve adjustment device which is designated the rotor 1, there are two magnets 2 and 3 with opposite polarity. The rotor 1 is held on a shaft 7. The shaft 7 is on the cover 18. The cover 18 bulges outward with respect to the valve. The rotor 1 is chucked by means of a screw 6 on the shaft 7 against the cover so that when the rotor 1 presses on the cover 18, there is a friction-tight connection between the rotor 1 and the cover 18, and the rotor 1 is prevented from any unintentional rotation. The friction-tight connection remains until an adjustment is made, as explained below. The friction-tight connection is strong enough to prevent any unintentional adjustment of the rotor, including by unforeseen magnetic fields.

The friction-tight connection is made on the outer edges of the rotor 1. That results from the outward curvature of the cover, and from the fact that the corresponding rotor surface is flat.

When pressure is applied to the cover 18, the cover experiences an elastic deformation. The cover becomes flat or even takes on a curvature in the opposite direction. The outer edges of the rotor thereby separate from the cover 18 and the rotor can be rotated by magnetic force.

The cover 18 is preferably from 0.1 to 0.2 mm thick, although in other exemplary embodiments it can be up to 0.5 mm thick. The deformation that is connected with the elastic bending preferably is 0.01 mm to approximately 0.1 mm, although in other exemplary embodiments it can be up to twice the thickness of the cover. The more the cover is biased, the more forcefully it must later be pressed from outside to effect a lifting of the rotor 1 at 6 from the cover 18 and to neutralize the locking of the rotor 1 on the cover 18.

The position of the rotor 1 defines the spring force that is applied in the opposite direction to compensate for gravity when the patient is in a standing position.

FIG. 2 shows a valve that is open on the bottom. The figure shows the spring 10, which is welded to the shaft 15 and the leaf spring 4. These components are preferably made from a metal material, in particular titanium or a titanium alloy. The spring wire of the spring 10 preferably has a diameter of 0.1 mm, although in other exemplary embodiments the spring wire can have a smaller cross section for shorter lengths and a greater cross section for longer lengths. In the illustrated exemplary embodiment, the cross section of the spring wire is circular. The leaf spring is preferably also 0.1 mm thick and approximately 1 mm high. The comments relating to the wire of spring 10 apply as appropriate for other exemplary embodiments with shorter lengths and with longer lengths. The leaf spring is very rigid.

On the left in the drawing, the shaft 7 has a shoulder and a stud with which it projects into a smaller boring of the part 9 on the rotor 1. When the device is assembled, there is a gap at the point 19 between the shaft 7 and the part 9. The gap is preferably 0.01 mm, although it can also be 0.1 mm or even more.

In FIG. 1, the skin side is on the left in the drawing and the inside of the body is on the bottom. If a pressure is now exerted mechanically from the outside through the skin on the cover 18, the cover 18 is deformed/curved toward the inside as a function of the force, and the shaft 7 is pushed downward toward the cover 20. As a result, the gap 19 is closed, the shaft 7 presses against part 9 and thus lifts the entire rotor from the cover 18. The elastic bias of the cover 18 and the friction forces at the point 8 are thereby overcome. Now there is a gap at the point 8 and the rotor can rotate freely. If the external load is then removed, the outer cover 18 returns to its initial position and generates the elastic bias between the contact point 17 and the contact point 8. The rotor is again clamped in the housing, and further rotation is impossible.

The rotor has a cam disc 13.

FIG. 2 shows the rotor 1 in the minimum position. As the result of a rotation by approximately 300 degrees, the spring 10 at the contact point 21, corresponding to the cam disc 13, is moved into its maximum position, so that the resulting opening pressure now becomes maximum. The height difference between the minimum and maximum spring bias of part 4 or 10 is approximately 0.7 to 0.8 mm. In concrete terms, however, this difference is determined by the dimension of the titanium wire selected.

The two magnets 2 and 3 are positioned so that a magnetic field applied externally can produce a maximum torsional moment.

In other words, the distance between the magnets in the illustrated exemplary embodiment is 7 mm, in another exemplary embodiment it can be 8 mm, and in still other exemplary embodiments it can be up to 20 mm. In concrete terms, this distance is determined by the outside dimensions of the housing. The circular housing preferably has a diameter of 14 mm, although in other exemplary embodiments it can have a diameter up to 19 mm, or even up to 31 mm, and is ergonomically shaped so that on one hand the position of the valve can be correctly determined from outside, while on the other hand so that the tissue that lies over the valve is not damaged. Therefore sharp edges are avoided.

The rotor has a tip 22 which is shown in FIG. 2. This tip strikes against the stop 14 at the minimum value and against stop 23 at the maximum value. In the exemplary embodiment, this stop prevents the maximum and minimum settings from overlapping and ensures that they remain easily distinguishable at all times. In other exemplary embodiments, a transition can also be provided.

The shaft 15 preferably has a diameter of 0.3 mm and can optionally have a tip on the top and bottom to minimize the bearing forces. On account of the construction described above, the rotor 1 can be rotated only when the cover 18 is pressed to the left in the drawing and the rotor 1 can thereby rotate freely. Under these conditions, a specific magnetic field must simultaneously be applied from the outside to ensure a rotation. If the load on the cover is then removed, the position of the rotor is fixed by elastic clamping. Then, if a differential pressure occurs between the inlet and the outlet of the valve, which is greater than the opening pressure of the valve, the ball is pushed out of its valve seat against the leaf spring and the valve is again opened. It thereby becomes possible for the cerebrospinal fluid to flow from the inlet to the outlet through the valve and a further pressure increase is prevented. The actual valve characteristic is defined by the rotational position of the rotor 1 and/or by the resulting position of the contact point 21 on the coil or on the cam disc 13. By an appropriate modification of the shape of the cam, a non-linear opening characteristic of the valve can be set as a function of the angle of rotation of the rotor 1. The rotor is preferably fabricated so that in all the starting positions of the rotor, a rotation of 10 degrees in one direction or the other results in the same change in the opening pressure of the valve. The location of the magnets 2 and 3 as far apart as possible has the advantage that the highest possible adjustment moments can be realized with the smallest possible magnetic forces. The neodymium magnets used here have a cylindrical shape with a diameter of 1 mm and a height of approximately 1.2 mm. The fabrication of the housing and rotor and the fabrication of the other components from titanium has the advantage that it becomes possible to set an ideal bearing clearance with precise fits and to systematically avoid undesired play, as well as undesirably elevated friction. For example, the shaft 7 preferably has a diameter of 1 mm; the clearance in position 24 between shaft 7 and rotor 1 is preferably achieved by a close clearance fit. Just such a clearance fit is provided for the bearing of the shaft 15 in the valve housing. This shaft 15 is mounted similar to a door hinge in the valve housing and makes possible the nearly friction-free rotation of the leaf spring 4 in the context of the opening and closing of the valve. The overall height of the valve is approximately 4.5 mm. Significantly lower overall heights are not necessarily desirable or even possible, because it must not be too difficult to locate the valve by feel.

Figure 3:
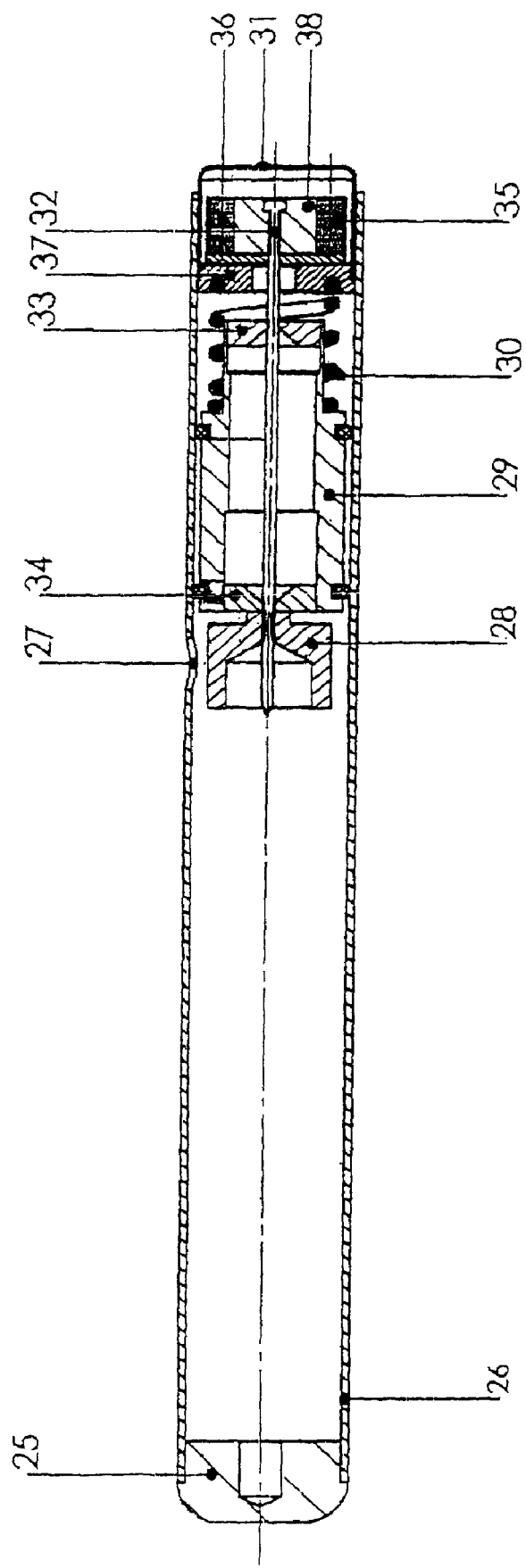
FIG. 3 shows an exemplary embodiment of an adjustment pin.

Special adjustment pins have been developed for the adjustment of the valve. One exemplary embodiment of such a pin is illustrated in FIG. 3. The illustration is enlarged compared to the illustration of the exemplary embodiment, although it is less of an enlargement than in FIGS. 1 and 2. To arrive at the correct size relationship between the valve and the pin as the adjustment device, the recommended method is to consider the pin in an enlargement that corresponds to the valve.

In a to-scale illustration, all the details would be so small that they would no longer be discernible.

A small, thin-walled tube 26 with a diameter of approximately 12 mm is closed on one end by a plug 25. A measurement mechanism on a needle bearing is installed on the other side. The measurement mechanism includes: measurement drum 28, on the surface of which a scale marking is applied, and the measurement drum is connected with the shaft 32 which is mounted in the bearing bush 29 at the positions 34 and 33. The bearing bush 29 is inserted into the small tube 26 so that it cannot be displaced or rotated. On the end of the small tube that is not closed, a movable cap is inserted into the tube and is pressed outward by a spring force. The spring 30 is supported on the bearing bush 29 and presses the ring 37 against the cap 31. The cylinder 38 is connected with the needle 32.

Magnets 35 and 36 are inserted into the cylinder 38. On the one magnet, the outboard pole is negative and on the other magnet it is positive. The distance between the magnets is approximately equal to the distance between the magnets inside the valve, i.e. the diameter.

The cap 31 and the spring 30 prevent a rotation of the shaft of the rotor and of the cylinder 38, as long as the cap is not pressed in the direction opposite to the spring force onto the bearing bush. Only when the pin is pushed above the valve against the patient's head, and thus the cap 31 presses into the pin housing, is a rotation of the rotor and scale drum and magnet cylinder possible. The pin must be pressed against the patient's head so that the window 27 can be viewed rotated by 90 degrees with respect to the axis of the patient's body. This arrangement ensures that the valve pin and the valve itself will be oriented in the same direction. If the cap above the valve is then pushed in front of or toward the front of the patient's head, the position of the rotor inside the pin follows the position of the rotor inside the valve, because the valve rotor cannot change its position as a result of the elastic clamping, although on account of the precision needle bearing in the positions 33 and 34, the position of the valve-side rotor can be adjusted by rotation. The corresponding settling pressure of the valve can then be read easily in the window 27. This construction guarantees a secure and easily reproducible measurement. As a result of the fixing of the measurement only a few tenths of a millimeter from the head, a twisting after the pin is removed from the patient's head is no longer possible. The measurement result is frozen immediately.

Figure 4:
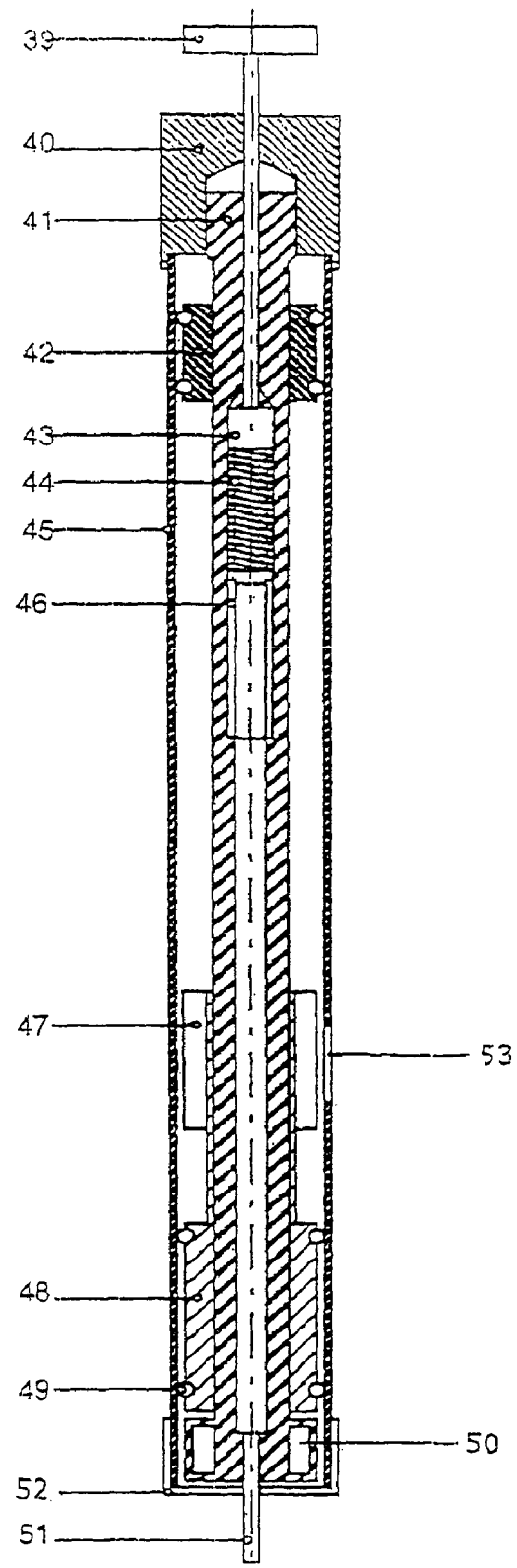
FIG. 4 shows an additional exemplary embodiment of an adjustment pin.

FIG. 4 shows an additional exemplary embodiment of an adjustment pin. The dimensions are approximately the same as the dimensions of a conventional ball-point pen, i.e. the small tube has an outside diameter of preferably 12 mm and a length of approximately 10 cm. The adjustment wheel 40 is permanently fixed in position on the shaft 41. A rotation of this wheel effects a rotation of the shaft. On the lower end of the shaft 41, two cylinder-shaped magnets 50 are introduced into the shaft. As in the valve, these magnets have different polarities. On the one magnet, the south pole is on the bottom, and on the other magnet the north pole is on the bottom. The position of the two magnets on the shaft corresponds to the position of the scale which appears on part 47. This scale is also permanently connected with the shaft 41. The bushing 48 acts as a bearing for the shaft 41. The bearing is introduced though O-rings, by which the bushing is fixed in position in the sleeve 45. A second bearing bush is attached to the upper area of the pin, part 42. Here, too, the shaft 41 is fixed in position and acts a friction bearing in the bushing 42. The adjustment pen contains two different springs: a strong spring 44 and an extremely weak spring 46. By pressing on the button 39, the shaft 41, which has a piston-like expanded portion in the lower portion, is pressed downward against the spring force 44. The shaft 51 is thereby pushed downward against the spring force of the significantly weaker spring 46. The spring 46 is therefore severely compressed, although on the other hand the spring 44 is compressed only a little. The force of the spring 44 is transmitted by the shaft 51 to its lower tip, which in this specific application is intended to exert the force on the valve to be adjusted. The diameter of the shaft at the tip should preferably be approximately 3 mm, and the lower end should be rounded in a dome-shape. The cap 52 installed in the lower end of the pin 52 protects the bearing and the magnets 50 installed in the shaft 41. The position of the magnets can be read through the window 53 via the scale on the scale drum 47. The construction of at least one possible embodiment makes it possible to build the adjustment unit so that it is extremely small without negatively impacting the security of the adjustment. For the first time it becomes possible to realize adjustment pens of this type. The construction therefore makes it possible to place the magnets extremely close to the patient's skin. A precise adjustment can be made by applying pressure simultaneously to the valve housing.

Figure 6:
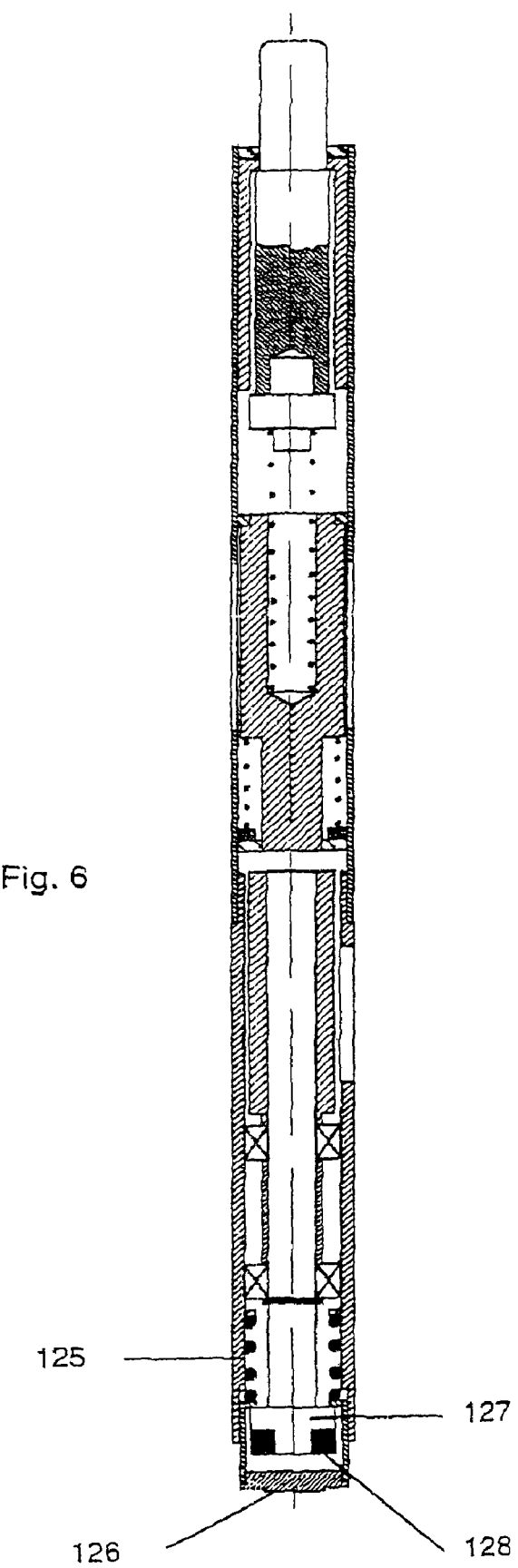
FIG. 6 shows at least one possible embodiment of an adjustment device.

The molding is rotated by means of an adjustment device of the type illustrated in FIG. 6. The adjustment device includes a housing 125 with a cap 126, with which the adjustment device is placed on the valve.

A head 127 with two pin magnets 128 is provided in the housing 125. The pin magnets 128 are at the same distance from each other as the magnets of the rotor 1, although they are arranged so that when the adjustment device is placed on the valve they point with opposite poles to the magnets of the molding. The magnets thereby attract each other and the rotor 1 tracks a rotation or a pivoting movement of the adjustment device with a rotation or pivoting motion in the same direction. The precise positioning of the adjustment device is also advantageously facilitated. With light contact, the attraction force of the magnets guides the adjustment device into the correct position.

Then the pressure applied is increased to cause a slight deformation of the valve housing. The housing cover is thereby elastically deformed. To facilitate the deformation, the cover 102 is provided with a deformation thickness. The deformation thickness in the illustrated exemplary embodiment is 0.2 mm. The consequence of the deformation is that the rotor 1 is lifted away from the associated friction surfaces. The friction is neutralized. The rotor can then be rotated or pivoted with corresponding ease.

A corresponding open space is created in the housing to take the deformation taught by the application into consideration.

One advantageous exemplary embodiment is illustrated in FIGS. 10 to 12.

In this embodiment, a disk-shaped valve with a ring-shaped housing 330 is provided. The housing 330 is provided with covers on both sides. The openings in the housing 330 corresponding to the covers allow the installation of all the parts provided in the valve.

The housing 330 is provided with a connecting pipe or socket 302 and a discharge pipe socket 312. The connecting pipe 203 is realized on the outside end as a connection for the hose line. On the inside, the connecting pipe extends through the housing wall 30 into the interior of the housing, so that in the interior of the housing a pipeline 314 that runs downward along the interior wall of the housing can be connected to the connecting pipe. At the same time, the inside end of the connecting pipe 302 is closed, so that all of the incoming fluid is forced into the pipeline 314.

The pipeline 314 leads to the discharge pipe 312, which is realized in parts so that it is similar to the connecting pipe 302. The discharge pipe 312 is installed in the same manner as the connecting pipe 302.

The discharge pipe 312, in contrast to the connecting pipe, forms a valve seat for a valve ball 310. The valve seat is in the shape of a conical boring. The pipeline 314 is connected to a feed boring 309 in the discharge pipe. The feed pipe 309 forms a connection from the pipeline 314 to the conical hole which, together with the sapphire sphere, forms the valve seat.

In the illustrated position of the valve, which is with the patient in a standing position the valve ball 310 presses against the valve seat. A cap 308 which is located in the valve housing so that it can pivot or rotate also presses on the valve ball 310. Consequently, the fluid flow must overcome the resistance of the valve ball 310 and of the cap 308 to exit upward out of the discharge tube. The fluid that emerges on the top flows into the housing 330 and from there through an opening 319, then via the exit opening 313 of the discharge pipe 312 into a downstream portion of the hose line (not shown).

FIGS. 11 and 12 show that the cap 308 comprises a cylindrical jacket which is provided on the end with a collar that is directed inward. The cap 308 encloses a cavity in which, in one exemplary embodiment, an adjustment device is located.

The cap 308, in the view in FIG. 11, has a clip. In the clip there is a boring for a bearing pin 317. The cap 308 is welded with the bearing journal 317 and is mounted so that it can pivot in the valve housing. Fastened to the bearing journal 217 is a wire spring 316, which in the illustrated exemplary embodiment is fastened by welding. Thus the cap 308, the spring 316 and the bearing journal 317 form a positive connection.

The spring wire 316 is guided through an opening in the cylindrical jacket of the cap 308 into its cavity. The opening has an opening width that is sufficient to allow a slight pivoting movement or deformation of the spring wire.

The deformation of the spring wire generates a torque on the bearing journal 317. The torque acts via the bearing journal 317 on the cap 308 and, when he patient is in the standing position, opposite to the weight of the cap 308.

The deformation of the spring wire is generated by means of a rotor 305. The rotor 305 is mounted rotationally on a shaft 304 which is fastened to a cover 331 of the housing. The cover 331 is curved outward. At the same time, the rotor 305 that sits on the journal 304 is braced by a screw or a locking ring 306 against the cover 331. The rotor 305 with its outer edges thereby touches the cover 331. The bracing has the advantage that a minimum pressure is necessary to release the brake or to release the lock, which minimum pressure is higher than conventional pressures that are exerted during daily life, e.g. the pressure exerted when the patient rises from a reclining position. This measure prevents the rotor 305 from unintentionally coming detached from the cover 331.

In addition, a slight deformation of the cover suffices to detach the rotor 305 from the cover for an adjustment.

The adjustment is made using two pin magnets 315 which are mounted in the rotor 305. The adjustment is made as described in the exemplary embodiments described above with other, external (percutaneous) magnets.

The spring wire 316 slides on a curved slip surface 333 of the rotor 305. In this exemplary embodiment, the slip surface 333 is designed so that as the rotor 305 rotates, a uniform change in the distance of the end of the wire with which it is contact takes place with respect to the center of the rotor. In the illustrated exemplary embodiment, that is equivalent to a uniform increase or reduction of the spring force. In other exemplary embodiments, another change in distance and another change in the spring force is provided.

One feature or aspect of an embodiment is believed at the time of the filing of this patent application to possibly reside broadly in an adjustable hydrocephalus valve to equalize the pressure of the liquor in the skull of a hydrocephalus patient, whereby the valve is implanted in the patient and the excess liquor is drained from the ventricles of the brain in the patient's skull via a hose line that is preferably implanted at the same time, and preferably into the superior vena cava or into the abdomen, whereby the valve comprises a valve housing with a closing part located in it, which in the closed position presses against the valve opening, whereby the valve pressure, at least when the patient is in the standing position, is at least partly determined by the weight of the movable closing part, which is preferably realized in the form of a ball, ring or disc, whereby when the patient is in the standing position, a percutaneously adjustable spring partly or completely compensates for the weight of the closing part.

Another feature or aspect of an embodiment is believed at the time of the filing of this patent application to possibly reside broadly in the adjustable hydrocephalus valve, whereby in addition to the closing part, a gravitation part is also provided in the valve housing and when the patient is in the standing position is in a non-positive connection with the closing part, whereby the spring is connected with the gravitation part and is adjustable so that the load of the gravitation part on the closing part in the standing position can be set, characterized in that the gravitation part is realized in the form of a disc or ring or cap or bell, and is located so that it can rotate or swivel in the valve housing.

Yet another feature or aspect of an embodiment is believed at the time of the filing of this patent application to possibly reside broadly in the adjustable hydrocephalus valve, characterized in that the gravitation part is formed by at least two balls, whereby when a ball is used for the closing part, the ball that forms the gravitation part is located, when the patient is in the standing position, above the ball for the closing part, and the spring is engaged with the ball that forms the gravitation part, preferably so that the spring is engaged between the two balls.

Still another feature or aspect of an embodiment is believed at the time of the filing of this patent application to possibly reside broadly in the adjustable hydrocephalus valve, characterized in that the adjustment device for the spring is located partly or completely inside the cavity of the ring or cap or bell.

A further feature or aspect of an embodiment is believed at the time of the filing of this patent application to possibly reside broadly in the adjustable hydrocephalus valve, characterized in that the closing part of the valve is located next to the ring or cap or bell and that the spring leads through an opening in the ring or cap or bell to the closing part.

Another feature or aspect of an embodiment is believed at the time of the filing of this patent application to possibly reside broadly in the adjustable hydrocephalus valve, characterized in that the gravitation part is guided in the valve housing.

Yet another feature or aspect of an embodiment is believed at the time of the filing of this patent application to possibly reside broadly in the adjustable hydrocephalus valve, characterized in that the guide is formed by a pivoting or rotating mounting or is a linear guide.

Still another feature or aspect of an embodiment is believed at the time of the filing of this patent application to possibly reside broadly in the adjustable hydrocephalus valve, characterized in that the gravitation part weighs more than the closing part.

A further feature or aspect of an embodiment is believed at the time of the filing of this patent application to possibly reside broadly in the adjustable hydrocephalus valve, characterized in that ruby, sapphire, titanium are used for the closing part and/or tantalum is used for the gravitation part.

Another feature or aspect of an embodiment is believed at the time of the filing of this patent application to possibly reside broadly in the adjustable hydrocephalus valve, characterized by a disc shape of the valve, whereby the gravitation part is located at a distance from the housing wall or from the housing floor or from the housing cover in the valve housing that is sufficient for its movement and at a distance from the internal fixtures in the valve housing that is sufficient for the movement.

Yet another feature or aspect of an embodiment is believed at the time of the filing of this patent application to possibly reside broadly in the adjustable hydrocephalus valve, characterized in that the valve housing has at least one cover and the disc or ring or cap or bell that forms the gravitation part has a diameter that is smaller than the opening in the valve housing that corresponds to the cover.

Still another feature or aspect of an embodiment is believed at the time of the filing of this patent application to possibly reside broadly in the adjustable hydrocephalus valve, characterized in that the spring is fastened in whole or in part to the pivot axis.

A further feature or aspect of an embodiment is believed at the time of the filing of this patent application to possibly reside broadly in the adjustable hydrocephalus valve, characterized in that the spring is realized in the form of a spring wire or in the form of a leaf spring.

Another feature or aspect of an embodiment is believed at the time of the filing of this patent application to possibly reside broadly in the adjustable hydrocephalus valve, characterized in that the spring is provided with an adjustment device.

Yet another feature or aspect of an embodiment is believed at the time of the filing of this patent application to possibly reside broadly in the adjustable hydrocephalus valve, characterized in that the adjustment device has a device that can rotate or pivot, which is rotated or pivoted from outside by means of magnets, so that the spring is placed under tension or relaxed.

Still another feature or aspect of an embodiment is believed at the time of the filing of this patent application to possibly reside broadly in the adjustable hydrocephalus valve, characterized by an brake that can be activated, the activation of which prevents an unintended adjustment movement, and the deactivation of which makes the adjustment movement possible.

A further feature or aspect of an embodiment is believed at the time of the filing of this patent application to possibly reside broadly in the adjustable hydrocephalus valve, characterized by a self-activated, spring-loaded brake which is deactivated by relaxation of the spring pressure.

Another feature or aspect of an embodiment is believed at the time of the filing of this patent application to possibly reside broadly in the adjustable hydrocephalus valve, characterized in that a) the valve housing is realized so that it is elastic and has friction surfaces which, when the valve housing is not subjected to any load, are in friction-tight contact with at least a portion of the adjustment device and are lifted up from the corresponding surfaces of the adjustment device by compressing the valve housing, or b) a valve housing is provided with a elastic cover which, when the valve housing is not subjected to any load, is in friction-tight contact with at least a portion of the adjustment device, and is lifted under pressure from the corresponding surfaces of the adjustment device.

Yet another feature or aspect of an embodiment is believed at the time of the filing of this patent application to possibly reside broadly in the adjustable hydrocephalus valve, characterized in that the elastic housing or the cover a) when the brake is in the locked position, an initial shape that is curved outward, and after the compression has a reduced curvature or a flat surface or an inward curvature; b) when the brake is in the locked position, has a flat initial shape and after the compression has an inward curvature; c) when the brake is in the locked position, has an inward curvature and after the compression assumes an increased inward curvature, or the housing wall has an inwardly curved initial shape and experienced a further inward curvature as a result of the deformation.

A further feature or aspect of an embodiment is believed at the time of the filing of this patent application to possibly reside broadly in the adjustable hydrocephalus valve, characterized by the use of an adjustment disc or rotor that is mounted so that it can rotate or pivot and has the friction surfaces for the locking on the outer periphery.

Another feature or aspect of an embodiment is believed at the time of the filing of this patent application to possibly reside broadly in the adjustable hydrocephalus valve, characterized by the use of an adjustment disc or rotor that is mounted so that it can rotate or pivot and is biased with the compressible housing wall and/or with the cover that can be depressed.

Yet another feature or aspect of an embodiment is believed at the time of the filing of this patent application to possibly reside broadly in the adjustable hydrocephalus valve, characterized by a deformation of the housing wall for the bias up to a dimension that is equal to twice the thickness of the housing wall, preferably up to 0.1 mm.

Still another feature or aspect of an embodiment is believed at the time of the filing of this patent application to possibly reside broadly in the adjustable hydrocephalus valve, characterized by the fact that an adjustment disc is used that has a U-shaped cross section so that the friction connection is made on the projecting edge of the U-shape.

A further feature or aspect of an embodiment is believed at the time of the filing of this patent application to possibly reside broadly in the adjustable hydrocephalus valve, characterized by the use of a housing wall that can be impressed or of a cover that can be impressed with a thickness up to 0.5 mm, preferably with a thickness up to 0.2 mm.

Another feature or aspect of an embodiment is believed at the time of the filing of this patent application to possibly reside broadly in the adjustable hydrocephalus valve, characterized in that the housing, preferably the deformable housing wall, is made of a metal, preferably of titanium or a titanium alloy.

Yet another feature or aspect of an embodiment is believed at the time of the filing of this patent application to possibly reside broadly in the adjustable hydrocephalus valve, characterized in that the valve device includes a rotational part with adjustment magnets that is applied percutaneously.

Still another feature or aspect of an embodiment is believed at the time of the filing of this patent application to possibly reside broadly in the adjustable hydrocephalus valve, characterized by a pressure control of the rotational part.

A further feature or aspect of an embodiment is believed at the time of the filing of this patent application to possibly reside broadly in the adjustable hydrocephalus valve, characterized by the use of spring elements for an indication of the pressure and the pressure limitation and/or the use of strain gauges to measure the pressure.

Another feature or aspect of an embodiment is believed at the time of the filing of this patent application to possibly reside broadly in the adjustable hydrocephalus valve, characterized by the use of magnets with a diameter of up to 3 mm, preferably a diameter of up to 1 mm and a height of up to 5 mm, preferably of a height of up to 2 mm.

Yet another feature or aspect of an embodiment is believed at the time of the filing of this patent application to possibly reside broadly in the adjustable hydrocephalus valve, characterized in that the magnets in the external adjustment device are at a distance from each other that differs from the magnets in the internal adjustment device by a maximum of 3 mm and preferably a maximum of 1 mm and/or that the magnets are at a distance from each other of 20 mm, preferably a maximum distance of 10 mm and even more preferably a maximum distance of 8 mm from each other.

Still another feature or aspect of an embodiment is believed at the time of the filing of this patent application to possibly reside broadly in the adjustable hydrocephalus valve, characterized in that the external adjustment device is provided with a measurement device for the adjustment movement.

A further feature or aspect of an embodiment is believed at the time of the filing of this patent application to possibly reside broadly in the adjustable hydrocephalus valve, characterized in that the measurement device is a measurement device that measures pressure and/or a device that measures rotation.

Another feature or aspect of an embodiment is believed at the time of the filing of this patent application to possibly reside broadly in the adjustable hydrocephalus valve, characterized in that the external adjustment device can be freely adjusted to the position of the magnet in the valve and that the rotational position of the magnets can be read externally.

Yet another feature or aspect of an embodiment is believed at the time of the filing of this patent application to possibly reside broadly in the adjustable hydrocephalus valve, characterized in that the internal adjustment device has a spring that is in the form of a metal wire or plate, the cross section of which is preferably round or rectangular, and the diameter or thickness of which is up to 0.5 mm, preferably up to 0.3 mm and even more preferably up to 0.2 mm.

Still another feature or aspect of an embodiment is believed at the time of the filing of this patent application to possibly reside broadly in the adjustable hydrocephalus valve, characterized in that the spring rod: a) is realized in the form of a one-armed lever, or b) is realized in the form of a two-armed lever, the one lever arm of which is effectively connected with the adjustment disc and the other lever arm of which is effectively connected with the valve ball or valve flap of the valve.

A further feature or aspect of an embodiment is believed at the time of the filing of this patent application to possibly reside broadly in the adjustable hydrocephalus valve, characterized in that the spring rod is mounted flexibly so that it presses in a sliding fashion against a cam disc of the adjustment disc and/or presses in a sliding fashion against the valve ball or valve flap of the valve.

Another feature or aspect of an embodiment is believed at the time of the filing of this patent application to possibly reside broadly in the adjustable hydrocephalus valve, characterized in that the valve has an outside diameter up to 31 mm, preferably up to 20 mm and/or a height of up to 10 mm, preferably up to 6 mm.

Yet another feature or aspect of an embodiment is believed at the time of the filing of this patent application to possibly reside broadly in the adjustable hydrocephalus valve, whereby the weight is positively connected with the spring element to be adjusted.

Another feature or aspect of an embodiment is believed at the time of the filing of this patent application to possibly reside broadly in a method of using the adjustable hydrocephalus valve, characterized in that the spring is provided with an adjustment device.

Yet another feature or aspect of an embodiment is believed at the time of the filing of this patent application to possibly reside broadly in a method of using the adjustable hydrocephalus valve, characterized in that the adjustment device has a device that can rotate or pivot, which is rotated or pivoted from outside by means of magnets, so that the spring is placed under tension or relaxed.

Still another feature or aspect of an embodiment is believed at the time of the filing of this patent application to possibly reside broadly in a method of using the adjustable hydrocephalus valve, characterized by an brake that can be activated, the activation of which prevents an unintended adjustment movement, and the deactivation of which makes the adjustment movement possible.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of methods or devices for treating hydrocephalus which may possibly be utilized or adapted for use in at least one possible embodiment may possibly be found in the following U.S. Pat. No. 6,882,876, entitled "Diagnosis of normal pressure hydrocephalus by automated processing of MR images;" U.S. Pat. No. 6,840,917, entitled "Implantable subcutaneous valve for the treatment of hydrocephalus, and adjusting devices therefor;" U.S. Pat. No. 6,540,727, entitled "Process for treating a patient with hydrocephalus utilizing an external medical draining system;" U.S. Pat. No. 6,283,934, entitled "Device for the treatment of hydrocephalus;" U.S. Pat. No. 6,193,682, entitled "Low profile neonatal hydrocephalus device and methods;" U.S. Pat. No. 6,146,352, entitled "Implantable drainage valve for the treatment of hydrocephalus;" U.S. Pat. No. 5,928,182, entitled "Pediatric programmable hydrocephalus valve;" U.S. Pat. No. 5,843,013, entitled "Valve for the treatment of hydrocephalus;" U.S. Pat. No. 5,728,061, entitled "Device and method for treating hydrocephalus;" U.S. Pat. No. 5,368,556, entitled "Implantable drainage valve for the treatment of hydrocephalus;" U.S. Pat. No. 5,207,684, entitled "Sheath for shunt placement for hydrocephalus;" U.S. Pat. No. 5,069,663, entitled "Hydrocephalus valve;" U.S. Pat. No. 5,000,731, entitled "Shunting device adopted in the intracranial shunting surgical operation for the treatment of hydrocephalus;" U.S. Pat. No. 4,787,887, entitled "Ventricular by-pass valve for draining the cephalorachidian liquid in the hydrocephalus;" U.S. Pat. No. 4,741,730, entitled "Hydrocephalus shunt with in-line filter;" U.S. Pat. No. 4,673,384, entitled "Valve for the treatment of hydrocephalus;" U.S. Pat. No. 4,588,085, entitled "Sterile air feedthrough packaging system for testing hydrocephalus shunt valves;" U.S. Pat. No. 4,443,214, entitled "Valve for the treatment of hydrocephalus;" U.S. Pat. No. 4,432,853, entitled "Method of making an ion beam sputter-etched ventricular catheter for hydrocephalus shunt;" U.S. Pat. No. 4,377,169, entitled "Ion beam sputter-etched ventricular catheter for hydrocephalus shunt;" and U.S. Pat. No. 4,375,816, entitled "Catheters for shunting systems for the treatment of hydrocephalus."

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of medical valves which may possible be utilized or adapted for use may possibly be found in the following U.S. Pat. No. 6,892,998, entitled "Medical valve and method of assembling the same;" U.S. Pat. No. 6,883,778, entitled "Apparatus for reducing fluid drawback through a medical valve;" U.S. Pat. No. 6,875,198, entitled "Surgical suction regulator valve;" U.S. Pat. No. 6,869,426, entitled "Anti-drawback medical valve;" U.S. Pat. No. 6,837,852, entitled "Control valve for suction device for surgical applications;" U.S. Pat. No. 6,805,688, entitled "Method and device for use in micro-invasive surgical procedures, and guide catheter and valve unit for a device for use in micro-invasive surgical procedures;" U.S. Pat. No. 6,802,490, entitled "Needle free medical connector with expanded valve mechanism and method of fluid flow control;" U.S. Pat. No. 6,790,237, entitled "Medical stent with a valve and related methods of manufacturing;" U.S. Pat. No. 6,767,340, entitled "Sealing valve assembly for medical products;" U.S. Pat. No. 6,764,494, entitled "Device for removal of an aorta valve at a human heart in course of a minimal surgical operation;" U.S. Pat. No. 6,755,391, entitled "Anti-drawback medical valve;" U.S. Pat. No. 6,712,791, entitled "Splittable medical valve;" U.S. Pat. No. 6,706,022, entitled "Needleless medical connector with expandable valve mechanism;" U.S. Pat. No. 6,695,817, entitled "Medical valve with positive flow characteristics;" U.S. Pat. No. 6,682,509, entitled "Medical valve and method of use;" U.S. Pat. No. 6,669,673, entitled "Medical valve;" U.S. Pat. No. 6,648,017, entitled "Valve arrangement for a medical apparatus;" U.S. Pat. No. 6,641,559, entitled "Buret with foot valve for medical infusion equipment;" U.S. Pat. No. 6,635,044, entitled "Medical valve with fluid escape space;" No. RE38,145, entitled "Luer-receiving medical valve;" U.S. Pat. No. 6,572,592, entitled "Medical valve and method of use;" U.S. Pat. No. 6,537,258, entitled "Valve for medical infusion lines and the like;" U.S. Pat. No. 6,506,197, entitled "Surgical method for affixing a valve to a heart using a looped suture combination;" U.S. Pat. No. 6,481,462, entitled "Medical flush valve;" U.S. Pat. No. 6,447,473, entitled "Medical suction valve;" U.S. Pat. No. 6,436,067, entitled "Powered surgical handpiece with suction conduit including a stepped valve to regulate flow through the suction conduit;" and U.S. Pat. No. 6,427,691, entitled "Medical valve."

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of shunt valves which may possibly be utilized or adapted for use in at least one possible embodiment may possibly be found in the following U.S. Pat. No. 6,666,208, entitled "Set for inserting a shunt valve into a shunt between the oesophagus and the trachea;" U.S. Pat. No. 6,358,222, entitled "Shunt valve;" U.S. Pat. No. 6,289,990, entitled "Production tubing shunt valve;" U.S. Pat. No. 6,255,806, entitled "Supply device for power supply to an electronic unit in a semiconductor valve in a shunt-connected thyristor-switched capacitor;" U.S. Pat. No. 6,029,703, entitled "Pressure solenoid control valve with flux shunt;" U.S. Pat. No. 6,007,511, entitled "Shunt valve and therapeutic delivery system for treatment of glaucoma and methods and apparatus for its installation;" U.S. Pat. No. 5,935,095, entitled "External slot valve for controlling blood flow through the outlet of a shunt of a cardiopulmonary bypass pump;" U.S. Pat. No. 5,304,114, entitled "Shunt valve system;" U.S. Pat. No. 5,042,974, entitled "Shunt valve;" U.S. Pat. No. 4,867,740, entitled "Multiple-membrane flow control valve and implantable shunt system;" U.S. Pat. No. 4,772,257, entitled "External programmer for magnetically-adjustable cerebrospinal fluid shunt valve;" U.S. Pat. No. 4,595,390, entitled "Magnetically-adjustable cerebrospinal fluid shunt valve;" U.S. Pat. No. 4,553,956, entitled "Shunt valve and method of use;" U.S. Pat. No. 4,551,128, entitled "Cerebrospinal fluid shunt valve;" U.S. Pat. No. 4,475,899, entitled "Shunt valve and method of use;" U.S. Pat. No. 4,387,715, entitled "Shunt valve;" U.S. Pat. No. 4,332,255, entitled "Shunt valve;" U.S. Pat. No. 4,094,145, entitled "Underspeed actuator for a hydrostatic transmission having a shunt valve;" U.S. Pat. No. 3,998,222, entitled "Subcutaneous arterio-venous shunt with valve;" U.S. Pat. No. 3,991,768, entitled "Shunt system resistant to overdrainage and siphoning and valve therefor;" and U.S. Pat. No. 3,985,140, entitled "Dual pressure valve for use in ventricular shunt system."

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . ." may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report, and/or cited elsewhere are hereby incorporated by reference as if set forth in their entirety herein as follows: DE19535637; EP0617975; FR2768057; and DE4401422.

U.S. application Ser. No. 11/149,928, filed Jun. 10, 2005 and having inventor Christoph MIETHKE, is hereby incorporated by reference as if set forth in its entirety herein.

The corresponding foreign and international patent publication applications, namely, Federal Republic of Germany Patent Application No. 10 2004 015 500.3, filed on Mar. 27, 2004, having inventor Christoph MIETHKE, and DE-OS 10 2004 015 500.3 and DE-PS 10 2004 015 500.3, and International Application No. PCT/EP2005/003052, filed on Mar. 22, 2005, having WIPO Publication No. WO2005/092424 and inventor Christoph MIETHKE, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. An adjustable hydrocephalus valve arrangement configured to be implanted subcutaneously in a hydrocephalus patient to equalize the pressure of the liquor in the skull of the patient by draining excess liquor from the ventricles of the brain in the skull of the patient, said arrangement comprising:

a valve being configured to control the pressure and flow of liquor through said valve arrangement;

a hose line being connected to said valve;

said hose line being configured to conduct liquor from the skull of the patient into the superior vena cava or into the abdomen of the patient;

said valve comprising:

a housing;

an inlet being configured and disposed to permit liquor to enter said housing;

an outlet being configured and disposed to permit liquor to exit said housing;

a closable valve opening being disposed between said inlet and said outlet;

a movable closing structure being disposed in said valve housing;

said movable closing structure comprising one of: a ball, a ring, and a disc;

said closing structure being configured, at least upon the patient being in an upright position, to be pressed by gravity against said valve opening to restrict flow of liquor through said valve opening and thus control the valve pressure, which valve pressure is at least partly determined by the weight of said closing structure;

a percutaneously adjustable spring being disposed in said housing;

an adjustment device being configured and disposed to adjust said adjustable spring;

said adjustable spring being configured and disposed to partly or completely compensate for the weight of said closing structure upon the patient being in an upright position;

said valve housing being at least partially elastic and comprising friction surfaces;

said adjustment device comprising friction surfaces;

said friction surfaces of said valve housing being configured and disposed to be in frictional contact with said friction surfaces of said adjustment device to thus minimize unintentional movement of said adjustment device upon said valve housing not being compressed; and said friction surfaces of said valve housing being configured and disposed to be in diminished frictional contact with said friction surfaces of said adjustment device to thus permit an adjustment movement of said adjustment device upon said valve housing being compressed.

2. The valve arrangement according to claim 1, wherein:

said closing structure comprises a gravitation part and a closing part;

said gravitation part comprises a disc or ring or cap, and is configured and disposed to rotate or swivel in the valve housing;

said gravitation part is configured and disposed, upon the patient being in an upright position, to be pressed by gravity against said closing part to thereby press said closing part against said valve opening; and said spring is connected with said gravitation part and is adjustable so that the load of said gravitation part on the closing part, upon the patient being in an upright position, can be set to partly or completely compensate for the weight of said gravitation part on said closing part.

3. The valve arrangement according to claim 2, wherein the adjustment device for the spring is located partly or completely inside a cavity in the gravitation part.

4. The valve arrangement according to claim 3, wherein the closing part of the valve is located next to the gravitation part and that the spring leads through an opening in the gravitation part to the closing part.

5. The valve arrangement according to claim 4, wherein the gravitation part is guided in the valve housing.

6. The valve arrangement according to claim 5, wherein the guide is formed by a pivoting or rotating mounting or is a linear guide, and the spring is fastened in whole or in part to the pivot axis.

7. The valve arrangement according to claim 6, wherein the gravitation part weighs more than the closing part.

8. The valve arrangement according to claim 7, wherein ruby, sapphire, or titanium is used for the closing part, and tantalum is used for the gravitation part.

9. The valve arrangement according to claim 8, wherein said valve has a disc shape, whereby the gravitation part is located at a distance from the housing wall or from the housing floor or from the housing cover in the valve housing that is sufficient for its movement and at a distance from the internal fixtures in the valve housing that is sufficient for the movement, and the valve housing has at least one cover, and the disc or ring or cap that forms the gravitation part has a diameter that is smaller than the opening in the valve housing that corresponds to the cover.

10. The valve arrangement according to claim 9, wherein the spring comprises a spring wire or a leaf spring; the spring is provided with an adjustment device; the adjustment device has a device that can rotate or pivot, which is rotated or pivoted from outside by means of magnets, so that the spring is placed under tension or relaxed; said arrangement comprises a brake that can be activated, the activation of which prevents an unintended adjustment movement, and the deactivation of which makes the adjustment movement possible; and said arrangement comprises a self-activated, spring-loaded brake which is deactivated by relaxation of the spring pressure.

11. The valve arrangement according to claim 10, wherein:

the valve housing is provided with an elastic cover which, when the valve housing is not subjected to any load, is in friction-tight contact with at least a portion of the adjustment device, and is lifted under pressure from the corresponding surfaces of the adjustment device; and the elastic housing or the cover:

c) when the brake is in the locked position, has an initial shape that is curved outward, and after the compression has a reduced curvature or a flat surface or an inward curvature;

d) when the brake is in the locked position, has a flat initial shape, and after the compression has an inward curvature; or e) when the brake is in the locked position, has an inward curvature, and after the compression assumes an increased inward curvature, or the housing wall has an inwardly curved initial shape and experienced a further inward curvature as a result of the deformation; and said arrangement is configured to use an adjustment disc or rotor that is mounted so that it can rotate or pivot and has the friction surfaces for the locking on the outer periphery; said arrangement is configured to use an adjustment disc or rotor that is mounted so that it can rotate or pivot and is biased with the compressible housing wall and/or with the cover that can be depressed; and said arrangement comprises a deformation of the housing wall for the bias up to a dimension that is equal to twice the thickness of the housing wall.

12. The valve arrangement according to claim 11, wherein an adjustment disc is used that has a U-shaped cross section so that the friction connection is made on the projecting edge of the U-shape; said arrangement is configured to use a housing wall that can be impressed or of a cover that can be impressed with a thickness up to 0.5 mm; wherein at least the deformable housing wall is made of a metal comprising: titanium or a titanium alloy; wherein the valve device includes a rotational part with adjustment magnets that is applied percutaneously; and wherein said arrangement comprises a pressure control of the rotational part.

13. The valve arrangement according to claim 12, wherein said arrangement is configured to use spring elements for an indication of the pressure and the pressure limitation and the use of strain gauges to measure the pressure; said arrangement is configured to use magnets with a diameter of up to 3 mm and a height of up to 5 mm; the magnets in the external adjustment device are at a distance from each other that differs from the magnets in the internal adjustment device by a maximum of 3 mm; the magnets in each device are at a distance from each other of a maximum distance of 20 mm; the external adjustment device is provided with a measurement device for the adjustment movement; and the measurement device is a measurement device that measures pressure and/or a device that measures rotation.

14. The valve arrangement according to claim 13, wherein the external adjustment device can be freely adjusted to the position of the magnet in the valve and that the rotational position of the magnets can be read externally; the internal adjustment device has a spring that comprises a metal wire or plate, the cross section of which is preferably round or rectangular, and the diameter or thickness of which is up to 0.5 mm;

the spring rod:

f) comprises a one-armed lever, or g) comprises a two-armed lever, the one lever arm of which is effectively connected with the adjustment disc and the other lever arm of which is effectively connected with the valve ball or valve flap of the valve; and the spring rod is mounted flexibly so that it presses in a sliding fashion against a cam disc of the adjustment disc and/or presses in a sliding fashion against the valve ball or valve flap of the valve; the valve has an outside diameter up to 31 mm and/or a height of up to 10 mm; and the weight is positively connected with the spring element to be adjusted.

15. The valve arrangement according to claim 1, wherein:
said closing structure comprises a gravitation part and a closing part;
said gravitation part comprises a ball;
said closing part comprises a ball;
said gravitation part is configured and disposed, upon the patient being in an upright position, to be pressed by gravity against said closing part to thereby press said closing part against said valve opening;
said spring is disposed between said gravitation part and said closing part and is engaged with said gravitation part; and
said spring is adjustable so that the load of the gravitation part on the closing part, upon the patient being in an upright position, can be set to partly or completely compensate for the weight of said gravitation part on said closing part.

16. The valve arrangement according to claim 15, wherein the spring comprises a spring wire or a leaf spring; the spring is provided with an adjustment device; the adjustment device has a device that can rotate or pivot, which is rotated or pivoted from outside by means of magnets, so that the spring is placed under tension or relaxed; said arrangement comprises a brake that can be activated, the activation of which prevents an unintended adjustment movement, and the deactivation of which makes the adjustment movement possible; and said arrangement comprises a self-activated, spring-loaded brake which is deactivated by relaxation of the spring pressure.

17. The valve arrangement according to claim 16, wherein:
a) the valve housing is elastic and has friction surfaces which, when the valve housing is not subjected to any load, are in friction-tight contact with at least a portion of the adjustment device and are lifted up from the corresponding surfaces of the adjustment device by compressing the valve housing, or
b) a valve housing is provided with a elastic cover which, when the valve housing is not subjected to any load, is in friction-tight contact with at least a portion of the adjustment device, and is lifted under pressure from the corresponding surfaces of the adjustment device; and
the elastic housing or the cover:
c) when the brake is in the locked position, has an initial shape that is curved outward, and after the compression has a reduced curvature or a flat surface or an inward curvature;
d) when the brake is in the locked position, has a flat initial shape, and after the compression has an inward curvature; or
e) when the brake is in the locked position, has an inward curvature, and after the compression assumes an increased inward curvature, or the housing wall has an inwardly curved initial shape and experienced a further inward curvature as a result of the deformation; and said arrangement is configured to use an adjustment disc or rotor that is mounted so that it can rotate or pivot and has the friction surfaces for the locking on the outer periphery; said arrangement is configured to use an adjustment disc or rotor that is mounted so that it can rotate or pivot and is biased with the compressible housing wall and/or with the cover that can be depressed; and said arrangement comprises a deformation of the housing wall for the bias up to a dimension that is equal to twice the thickness of the housing wall.

18. The valve arrangement according to claim 17, wherein an adjustment disc is used that has a U-shaped cross section so that the friction connection is made on the projecting edge of the U-shape; said arrangement is configured to use a housing wall that can be impressed or of a cover that can be impressed with a thickness up to 0.5 mm; wherein at least the deformable housing wall is made of a metal comprising: titanium or a titanium alloy; wherein the valve device includes a rotational part with adjustment magnets that is applied percutaneously; wherein said arrangement comprises a pressure control of the rotational part; said arrangement is configured to use spring elements for an indication of the pressure and the pressure limitation and the use of strain gauges to measure the pressure; said arrangement is configured to use magnets with a diameter of up to 3 mm and a height of up to 5 mm; the magnets in the external adjustment device are at a distance from each other that differs from the magnets in the internal adjustment device by a maximum of 3 mm; the magnets in each device are at a distance from each other of a maximum distance of 20 mm; the external adjustment device is provided with a measurement device for the adjustment movement; and the measurement device is a measurement device that measures pressure and/or a device that measures rotation; the external adjustment device can be freely adjusted to the position of the magnet in the valve and that the rotational position of the magnets can be read externally; the internal adjustment device has a spring that comprises a metal wire or plate, the cross section of which is preferably round or rectangular, and the diameter or thickness of which is up to 0.5 mm;
the spring rod:
f) comprises a one-armed lever, or
g) comprises a two-armed lever, the one lever arm of which is effectively connected with the adjustment disc and the other lever arm of which is effectively connected with the valve ball or valve flap of the valve; and
the spring rod is mounted flexibly so that it presses in a sliding fashion against a cam disc of the adjustment disc and/or presses in a sliding fashion against the valve ball or valve flap of the valve; the valve has an outside diameter up to 31 mm and/or a height of up to 10 mm; and the weight is positively connected with the spring element to be adjusted.

19. The valve arrangement according to claim 1, wherein said adjustment device comprises an internal adjustment device disposed in said valve housing.

20. The valve arrangement according to claim 19, wherein said internal adjustment device comprises a rotor.

* * * * *